United States Patent
Alster et al.

(10) Patent No.: US 9,421,126 B2
(45) Date of Patent: Aug. 23, 2016

(54) ANTERIOR SEGMENT DRUG DELIVERY

(75) Inventors: Yair Alster, Palo Alto, CA (US);
Eugene de Juan, Jr., San Francisco, CA (US); Cary J. Reich, Los Gatos, CA (US); Stephen Boyd, Murrieta, CA (US); David Sierra, Aptos, CA (US); Jose D. Alejandro, Sunnyvale, CA (US); K. Angela Macfarlane, Menlo Park, CA (US); Douglas Sutton, Pacifica, CA (US)

(73) Assignee: ForSight Vision5, Inc., Menlo Park, CA (US)

( * ) Notice: Subject to any disclaimer, the term of this patent is extended or adjusted under 35 U.S.C. 154(b) by 0 days.

(21) Appl. No.: 13/151,001

(22) Filed: Jun. 1, 2011

(65) Prior Publication Data

US 2012/0136322 A1     May 31, 2012

Related U.S. Application Data

(60) Provisional application No. 61/183,839, filed on Jun. 3, 2009.

(51) Int. Cl.
*A61F 9/00* (2006.01)
*A61M 35/00* (2006.01)
(Continued)

(52) U.S. Cl.
CPC ............. *A61F 9/0017* (2013.01); *A61F 9/0026* (2013.01); *A61K 9/0051* (2013.01); *A61K 31/19* (2013.01); *A61K 31/407* (2013.01); *A61K 31/4178* (2013.01); *A61K 31/43* (2013.01); *A61K 31/5377* (2013.01); *A61K 31/5415* (2013.01); *A61K 31/55* (2013.01); *A61K 31/557* (2013.01); *A61K 31/5575* (2013.01);
(Continued)

(58) Field of Classification Search
None
See application file for complete search history.

(56) References Cited

U.S. PATENT DOCUMENTS

| | | |
|---|---|---|
| 3,113,076 A | 12/1963 | Jacobs |
| 3,312,215 A | 4/1967 | Silber et al. |
| 3,416,530 A | 12/1968 | Ness |
| 3,545,439 A | 12/1970 | Kalamazoo et al. |
| 3,566,874 A | 3/1971 | Shepherd et al. |

(Continued)

FOREIGN PATENT DOCUMENTS

| | | |
|---|---|---|
| CN | 1003339058 C | 9/2007 |
| EP | 1473003 A2 | 11/2004 |

(Continued)

OTHER PUBLICATIONS

U.S. Appl. No. 13/366,165, filed Feb. 3, 2012.
(Continued)

*Primary Examiner* — Bethany Barham
*Assistant Examiner* — Dominic Lazaro
(74) *Attorney, Agent, or Firm* — Mintz Levin Cohn Ferris Glovsky and Popeo, P.C.

(57) ABSTRACT

A therapeutic system comprises an ocular insert placed on a region outside an optical zone of an eye. The ocular insert comprises two structures: a first skeletal structure and a second cushioning structure. The first structure functions as a skeletal frame which maintains positioning of the implant along the anterior portion of the eye and provides support to the second, cushioning structure. This first structure maintains the attachment of the therapeutic system to the anterior portion of the eye for at least thirty days. In some embodiments the first structure remains a constant size and shape, e.g. a ring shape, a ring with haptics, or a curvilinear ring that is confined to and restrainingly engages the inferior and superior conjunctival fornices so as to retain the implant within the tear fluid and/or against the tissues of the eye.

30 Claims, 17 Drawing Sheets

(51) Int. Cl.

| | | |
|---|---|---|
| *A61K 9/00* | (2006.01) | |
| *A61K 31/19* | (2006.01) | |
| *A61K 31/407* | (2006.01) | |
| *A61K 31/4178* | (2006.01) | |
| *A61K 31/5377* | (2006.01) | |
| *A61K 31/5415* | (2006.01) | |
| *A61K 31/43* | (2006.01) | |
| *A61K 31/55* | (2006.01) | |
| *A61K 31/557* | (2006.01) | |
| *A61K 31/5575* | (2006.01) | |
| *A61K 31/56* | (2006.01) | |
| *A61K 31/568* | (2006.01) | |
| *A61K 31/573* | (2006.01) | |
| *A61K 31/58* | (2006.01) | |
| *A61K 31/7036* | (2006.01) | |
| *A61K 38/00* | (2006.01) | |
| *A61M 31/00* | (2006.01) | |

(52) U.S. Cl.
CPC ............... *A61K31/56* (2013.01); *A61K 31/568* (2013.01); *A61K 31/573* (2013.01); *A61K 31/58* (2013.01); *A61K 31/7036* (2013.01); *A61K 38/00* (2013.01); *A61M 31/002* (2013.01)

(56) References Cited

U.S. PATENT DOCUMENTS

| | | | |
|---|---|---|---|
| 3,618,604 A | 11/1971 | Ness | |
| 3,626,940 A | 12/1971 | Zaffaroni | |
| 3,710,796 A | 1/1973 | Neefe | |
| 3,760,805 A | 9/1973 | Higuchi | |
| 3,811,444 A | 5/1974 | Heller et al. | |
| 3,826,258 A | 7/1974 | Abraham | |
| 3,828,777 A | 8/1974 | Ness | |
| 3,845,201 A | 10/1974 | Haddad et al. | |
| 3,867,519 A | 2/1975 | Micheals | |
| 3,903,880 A | 9/1975 | Higuchi | |
| 3,916,899 A | 11/1975 | Theeuwes | |
| 3,920,805 A | 11/1975 | Roseman | |
| 3,926,188 A | 12/1975 | Baker et al. | |
| 3,960,150 A | 6/1976 | Hussain | |
| 3,961,628 A | 6/1976 | Arnold | |
| 3,962,414 A | 6/1976 | Michaels | |
| 3,963,025 A | 6/1976 | Whitaker et al. | |
| 3,991,760 A | 11/1976 | Drobish et al. | |
| 3,993,073 A | 11/1976 | Zaffaroni | |
| 3,995,633 A | 12/1976 | Gougeon | |
| 3,995,634 A | 12/1976 | Drobish | |
| 3,995,635 A * | 12/1976 | Higuchi et al. ............... 424/427 |
| 4,008,719 A | 2/1977 | Theeuwes et al. | |
| 4,012,496 A | 3/1977 | Schopflin | |
| 4,014,334 A | 3/1977 | Theeuwes et al. | |
| 4,014,335 A | 3/1977 | Arnold | |
| 4,016,251 A | 4/1977 | Higuchi et al. | |
| 4,052,505 A | 10/1977 | Higuchi et al. | |
| 4,057,619 A | 11/1977 | Higuchi et al. | |
| 4,067,961 A | 1/1978 | Laughlin | |
| 4,093,709 A | 6/1978 | Choi et al. | |
| 4,131,648 A | 12/1978 | Choi et al. | |
| 4,155,991 A | 5/1979 | Schopflin et al. | |
| 4,157,864 A | 6/1979 | Koller et al. | |
| 4,160,452 A | 7/1979 | Theeuwes | |
| 4,164,560 A | 8/1979 | Folkman et al. | |
| 4,177,256 A | 12/1979 | Michaels et al. | |
| 4,179,497 A | 12/1979 | Cohen et al. | |
| 4,190,642 A | 2/1980 | Gale et al. | |
| 4,201,210 A | 5/1980 | Hughes et al. | |
| 4,215,691 A | 8/1980 | Wong | |
| 4,249,531 A | 2/1981 | Heller et al. | |
| 4,281,654 A | 8/1981 | Shell et al. | |
| 4,285,987 A | 8/1981 | Ayer et al. | |
| 4,292,965 A | 10/1981 | Nash et al. | |
| 4,303,637 A | 12/1981 | Shell et al. | |
| 4,304,765 A | 12/1981 | Shell et al. | |
| 4,322,323 A | 3/1982 | Capozza | |
| 4,343,787 A | 8/1982 | Katz | |
| 4,432,964 A | 2/1984 | Shell et al. | |
| 4,439,198 A | 3/1984 | Brightman | |
| 4,469,671 A | 9/1984 | Zimmerman et al. | |
| 4,484,922 A | 11/1984 | Rosenwald | |
| 4,524,776 A | 6/1985 | Withers | |
| 4,540,417 A * | 9/1985 | Poler ............................ 424/429 |
| 4,652,099 A | 3/1987 | Lichtman | |
| 4,678,466 A | 7/1987 | Rosenwald | |
| 4,822,616 A | 4/1989 | Zimmermann et al. | |
| 4,888,074 A | 12/1989 | Pocknell | |
| 4,961,931 A | 10/1990 | Wong | |
| 4,973,304 A | 11/1990 | Graham et al. | |
| 5,071,657 A | 12/1991 | Oloff et al. | |
| 5,098,443 A | 3/1992 | Parel et al. | |
| 5,137,728 A | 8/1992 | Bawa | |
| 5,147,647 A | 9/1992 | Darougar | |
| 5,178,635 A | 1/1993 | Gwon et al. | |
| 5,205,611 A | 4/1993 | Stephens | |
| 5,248,700 A | 9/1993 | Lance | |
| 5,300,114 A | 4/1994 | Gwon et al. | |
| 5,314,419 A | 5/1994 | Pelling | |
| 5,322,691 A * | 6/1994 | Darougar et al. ............. 424/427 |
| 5,370,607 A | 12/1994 | Memmen | |
| 5,378,475 A | 1/1995 | Smith et al. | |
| 5,395,618 A | 3/1995 | Darougar | |
| 5,443,505 A | 8/1995 | Wong et al. | |
| 5,472,436 A | 12/1995 | Fremstad | |
| 5,474,780 A | 12/1995 | Chang | |
| 5,476,511 A | 12/1995 | Gwon | |
| 5,496,811 A * | 3/1996 | Aviv et al. .................... 514/78 |
| 5,605,696 A | 2/1997 | Eury et al. | |
| 5,618,274 A | 4/1997 | Rosenthal | |
| 5,694,947 A | 12/1997 | Lehtinen et al. | |
| 5,773,019 A | 6/1998 | Ashton et al. | |
| 5,773,021 A | 6/1998 | Gurtler et al. | |
| 5,788,977 A | 8/1998 | Aguadisch et al. | |
| 5,824,086 A | 10/1998 | Silvestrini | |
| 5,851,547 A | 12/1998 | Fujioka et al. | |
| 5,855,906 A | 1/1999 | McClay | |
| 5,902,598 A | 5/1999 | Chen et al. | |
| 5,972,372 A | 10/1999 | Saleh et al. | |
| 5,989,579 A | 11/1999 | Darougar et al. | |
| 6,001,386 A | 12/1999 | Ashton et al. | |
| 6,015,213 A | 1/2000 | Nakada | |
| 6,096,076 A | 8/2000 | Silvestrini | |
| 6,109,537 A | 8/2000 | Heath | |
| 6,120,460 A | 9/2000 | Abreu | |
| 6,146,366 A | 11/2000 | Schachar | |
| 6,149,685 A | 11/2000 | Sigoloff | |
| 6,217,896 B1 | 4/2001 | Benjamin | |
| 6,264,971 B1 | 7/2001 | Darougar | |
| 6,361,780 B1 | 3/2002 | Ley et al. | |
| 6,375,642 B1 | 4/2002 | Grieshaber et al. | |
| 6,375,972 B1 | 4/2002 | Guo et al. | |
| 6,394,094 B1 | 5/2002 | McKenna et al. | |
| 6,485,735 B1 | 11/2002 | Steen et al. | |
| 6,547,714 B1 | 4/2003 | Dailey | |
| 6,634,576 B2 | 10/2003 | Verhoff et al. | |
| 6,669,950 B2 | 12/2003 | Yaacobi | |
| 6,719,750 B2 | 4/2004 | Varner et al. | |
| 6,746,686 B2 | 6/2004 | Hughes et al. | |
| 6,841,574 B2 | 1/2005 | Mo et al. | |
| 6,939,569 B1 | 9/2005 | Green et al. | |
| 6,964,781 B2 | 11/2005 | Brubaker | |
| 6,966,927 B1 | 11/2005 | Silverstrini | |
| 6,986,900 B2 | 1/2006 | Yaacobi | |
| 6,991,808 B2 * | 1/2006 | Brubaker et al. .............. 424/473 |
| 7,094,226 B2 | 8/2006 | Yaacobi | |
| 7,195,774 B2 | 3/2007 | Carvalho et al. | |
| 7,488,343 B2 | 2/2009 | O'Brien et al. | |
| 7,544,371 B2 | 6/2009 | Kunzler et al. | |
| 7,785,578 B2 | 8/2010 | Miller et al. | |
| 7,799,336 B2 | 9/2010 | Hughes | |
| 7,833,545 B2 | 11/2010 | Ron | |
| 7,862,552 B2 | 1/2011 | McIntyre et al. | |
| 7,910,126 B2 | 3/2011 | Ahmed et al. | |

(56) References Cited

U.S. PATENT DOCUMENTS

| | | | |
|---|---|---|---|
| 7,985,208 B2 | 7/2011 | Christensen | |
| 7,998,497 B2 | 8/2011 | de Juan, Jr. et al. | |
| 8,021,680 B2 | 9/2011 | Anderson et al. | |
| 2002/0026176 A1 | 2/2002 | Varner et al. | |
| 2002/0047058 A1 | 4/2002 | Verhoff et al. | |
| 2002/0115985 A1 | 8/2002 | Larson et al. | |
| 2003/0088307 A1 | 5/2003 | Shulze et al. | |
| 2003/0176854 A1 | 9/2003 | Rodstrom | |
| 2004/0042073 A1 | 3/2004 | Pynson | |
| 2004/0115234 A1 | 6/2004 | Gewirtz | |
| 2004/0121014 A1 | 6/2004 | Guo et al. | |
| 2004/0133155 A1 | 7/2004 | Varner et al. | |
| 2004/0170685 A1 | 9/2004 | Carpenter et al. | |
| 2004/0220660 A1 | 11/2004 | Shanley et al. | |
| 2004/0241243 A1 | 12/2004 | Lin et al. | |
| 2004/0249364 A1 | 12/2004 | Kaploun | |
| 2004/0265355 A1 | 12/2004 | Shalaby | |
| 2005/0019371 A1 | 1/2005 | Anderson et al. | |
| 2005/0042292 A1 | 2/2005 | Muldoon et al. | |
| 2005/0048099 A1 | 3/2005 | Shiah et al. | |
| 2005/0053639 A1 | 3/2005 | Shalaby | |
| 2005/0060021 A1 | 3/2005 | O'Brien et al. | |
| 2005/0125059 A1 | 6/2005 | Pinchuk et al. | |
| 2005/0163844 A1 | 7/2005 | Ashton | |
| 2005/0196424 A1 | 9/2005 | Chappa | |
| 2005/0197651 A1 | 9/2005 | Chen et al. | |
| 2005/0228473 A1 | 10/2005 | Brown | |
| 2005/0228482 A1 | 10/2005 | Herzog et al. | |
| 2005/0244461 A1 | 11/2005 | Nivaggioli et al. | |
| 2005/0244464 A1 | 11/2005 | Hughes | |
| 2005/0276841 A1 | 12/2005 | Davis et al. | |
| 2006/0024350 A1 | 2/2006 | Varner et al. | |
| 2006/0034891 A1 | 2/2006 | Lawin et al. | |
| 2006/0140867 A1 | 6/2006 | Helfer et al. | |
| 2006/0185678 A1 | 8/2006 | Bronnenkant et al. | |
| 2006/0212115 A1 | 9/2006 | Maldonado Bas | |
| 2006/0216328 A1 | 9/2006 | Kis et al. | |
| 2006/0235513 A1 | 10/2006 | Price | |
| 2006/0246112 A1 | 11/2006 | Snyder et al. | |
| 2006/0264912 A1 | 11/2006 | McIntyre et al. | |
| 2006/0292222 A1 | 12/2006 | Jonasse | |
| 2007/0112318 A1 | 5/2007 | Leahy | |
| 2007/0134305 A1 | 6/2007 | Zilberman | |
| 2007/0196433 A1 | 8/2007 | Ron et al. | |
| 2007/0202150 A1 | 8/2007 | Dave | |
| 2007/0212387 A1 | 9/2007 | Patravale et al. | |
| 2007/0243230 A1 | 10/2007 | de Juan et al. | |
| 2007/0269487 A1 * | 11/2007 | de Juan et al. | 424/427 |
| 2008/0090911 A1 | 4/2008 | Frank et al. | |
| 2008/0097591 A1 | 4/2008 | Savage et al. | |
| 2008/0103584 A1 | 5/2008 | Su et al. | |
| 2008/0145406 A1 | 6/2008 | Asgharian et al. | |
| 2008/0181930 A1 | 7/2008 | Rodstrom et al. | |
| 2008/0243095 A1 | 10/2008 | Kaiser | |
| 2009/0005864 A1 | 1/2009 | Eggleston | |
| 2009/0012836 A1 | 1/2009 | Weissbach et al. | |
| 2009/0081278 A1 | 3/2009 | De Graaff | |
| 2009/0082863 A1 | 3/2009 | Schieber et al. | |
| 2009/0092654 A1 | 4/2009 | De Juan, Jr. et al. | |
| 2009/0104243 A1 | 4/2009 | Utkhede et al. | |
| 2009/0104248 A1 | 4/2009 | Rapacki et al. | |
| 2009/0143752 A1 | 6/2009 | Higuchi et al. | |
| 2009/0148485 A1 | 6/2009 | Whitehead | |
| 2009/0155326 A1 | 6/2009 | Mack | |
| 2009/0155338 A1 | 6/2009 | Conway et al. | |
| 2009/0162417 A1 | 6/2009 | Eells | |
| 2009/0196903 A1 | 8/2009 | Kliman | |
| 2009/0220573 A1 | 9/2009 | Kaufman | |
| 2009/0234005 A1 | 9/2009 | Ishida et al. | |
| 2009/0234449 A1 | 9/2009 | De Juan, Jr. et al. | |
| 2009/0252807 A1 | 10/2009 | Jenkins et al. | |
| 2009/0280158 A1 | 11/2009 | Butuner | |
| 2009/0287300 A1 | 11/2009 | Dave et al. | |
| 2009/0291120 A1 | 11/2009 | Tuominen et al. | |
| 2009/0318549 A1 | 12/2009 | Butuner | |
| 2010/0040671 A1 | 2/2010 | Ahmed et al. | |
| 2010/0055139 A1 | 3/2010 | Lee | |
| 2010/0069857 A1 | 3/2010 | Christensen | |
| 2010/0074942 A1 | 3/2010 | Ratner et al. | |
| 2010/0114309 A1 | 5/2010 | de Juan, Jr. et al. | |
| 2010/0124565 A1 | 5/2010 | Spada et al. | |
| 2010/0166841 A1 | 7/2010 | Roth et al. | |
| 2010/0178316 A1 | 7/2010 | Chauhan et al. | |
| 2010/0209477 A1 | 8/2010 | Butuner et al. | |
| 2010/0209478 A1 | 8/2010 | Sawhney et al. | |
| 2010/0226962 A1 | 9/2010 | Rodstrom | |
| 2010/0233241 A1 | 9/2010 | Leahy et al. | |
| 2010/0266664 A1 | 10/2010 | Asgharian et al. | |
| 2010/0278898 A1 | 11/2010 | Hughes et al. | |
| 2010/0331796 A1 | 12/2010 | Leahy et al. | |
| 2011/0009958 A1 | 1/2011 | Wardle et al. | |
| 2011/0105986 A1 | 5/2011 | Bronstein et al. | |
| 2011/0184358 A1 | 7/2011 | Weiner | |
| 2011/0195123 A1 | 8/2011 | Shemi | |
| 2011/0268783 A1 | 11/2011 | Shalaby et al. | |
| 2011/0280909 A1 | 11/2011 | Moazed | |
| 2011/0282328 A1 | 11/2011 | Ambati et al. | |
| 2012/0022473 A1 | 1/2012 | Shikamura et al. | |
| 2012/0089072 A1 | 4/2012 | Cunningham, Jr. | |
| 2012/0109054 A1 | 5/2012 | Thompson et al. | |
| 2012/0136322 A1 | 5/2012 | Alster et al. | |
| 2012/0168422 A1 | 7/2012 | Boyd et al. | |
| 2012/0177716 A1 | 7/2012 | Ho et al. | |
| 2012/0187594 A1 | 7/2012 | Utkhede et al. | |
| 2012/0215184 A1 | 8/2012 | Lim | |
| 2012/0245505 A1 | 9/2012 | Robinson et al. | |
| 2012/0269893 A1 | 10/2012 | Lee | |
| 2013/0090612 A1 | 4/2013 | de Juan, Jr. et al. | |
| 2013/0142858 A1 | 6/2013 | Kopczynski et al. | |
| 2013/0144128 A1 | 6/2013 | de Juan, Jr. et al. | |
| 2013/0177615 A1 | 7/2013 | Lee | |
| 2013/0209538 A1 | 8/2013 | Venkatraman et al. | |
| 2013/0261569 A1 | 10/2013 | Weiner et al. | |
| 2014/0121612 A1 | 5/2014 | Rubin et al. | |
| 2015/0133878 A1 | 5/2015 | de Juan, Jr. et al. | |

FOREIGN PATENT DOCUMENTS

| | | |
|---|---|---|
| GB | 1372944 | 11/1974 |
| GB | 1529143 A | 10/1977 |
| JP | S5560452 | 5/1980 |
| JP | 2007167358 | 7/2007 |
| WO | WO 97/43984 * | 11/1997 |
| WO | WO-02/076426 A2 | 10/2002 |
| WO | WO-2007083293 A1 | 7/2007 |
| WO | WO 2009/035562 A2 | 3/2009 |
| WO | WO 2010/141729 A1 | 12/2010 |
| WO | PCT/US12/23875 | 2/2012 |
| WO | PCT/US12/55532 | 9/2012 |
| WO | PCT/US2012/55532 | 9/2012 |
| WO | PCT/US2013/066834 | 10/2013 |
| WO | PCT/US2014/031955 | 3/2014 |
| WO | PCT/US2014/060244 | 10/2014 |

OTHER PUBLICATIONS

U.S. Appl. No. 13/618,052, filed Sep. 14, 2012.
U.S. Appl. No. 61/568,624, filed Dec. 8, 2011.
International Search Report and Written Opinion of PCT Application No. PCT/US2010/037268 mailed on Jul. 21, 2010, 8 pages.
U.S. Appl. No. 61/534,845, filed Sep. 14, 2011.
Kawakita et al.,"Measurement of fornix depth and area: a novel method of determining the severity of fornix shortening", Eye (2009) 23, 1115-1119.
International Search Report and Written Opinion of PCT Application No. PCT/US2012/055532. Feb. 26, 2013.
Zeus Technical Newsletter. "Strength and Stiffness of Plastics". (Obtained from http://www.zeusinc.com/UserFiles/zeusinc/Documents/technical_newsletters/Zeus_StrengthStiffnessPlastics.pdf on Oct. 18, 2013).

* cited by examiner

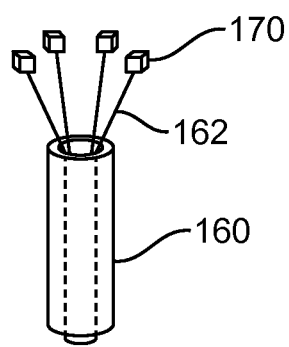
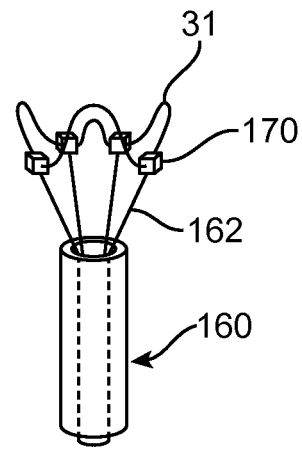
FIG. 13-1         FIG. 13-2
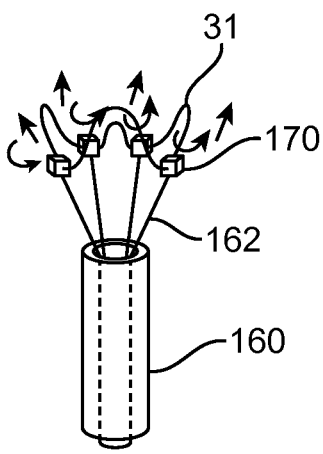
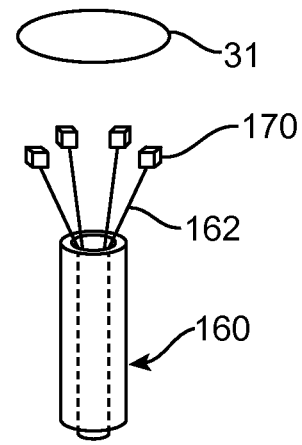
FIG. 13-3         FIG. 13-4

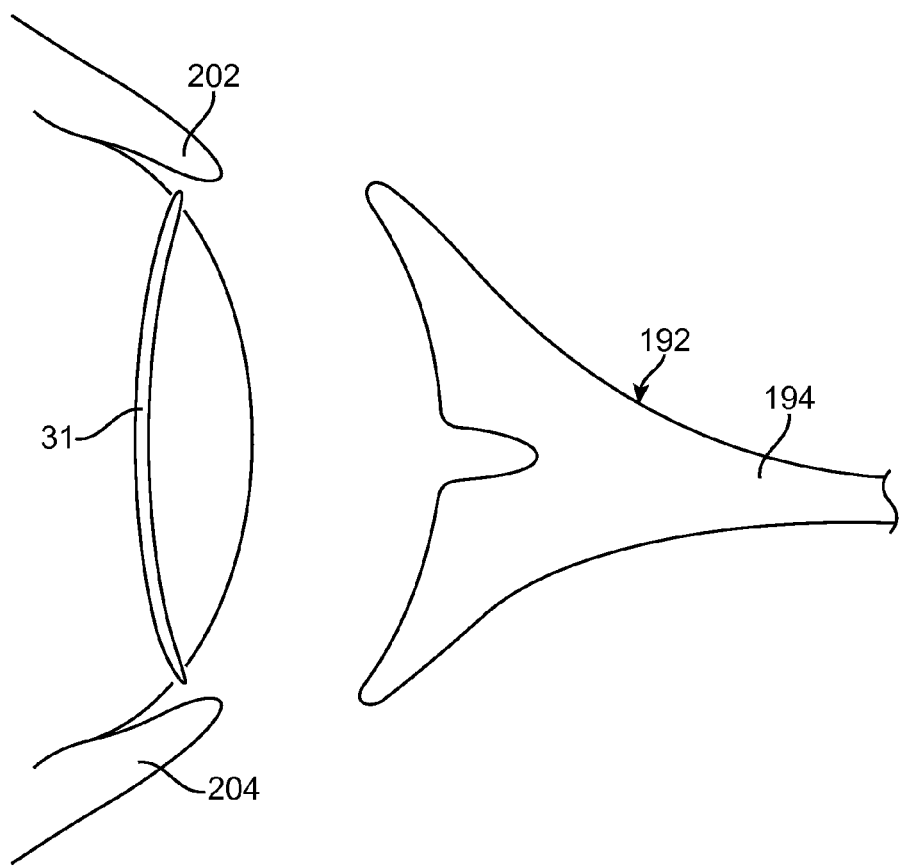
FIG. 16-6
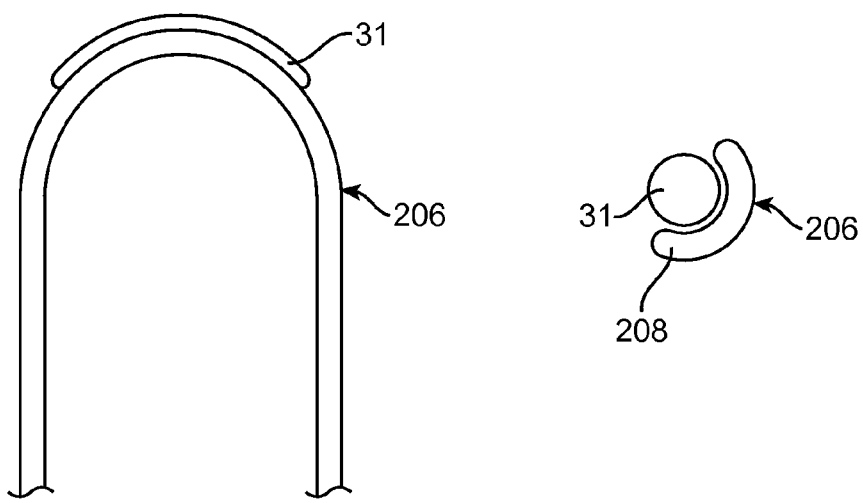
FIG. 17-1
FIG. 17-2

ANTERIOR SEGMENT DRUG DELIVERY

CROSS-REFERENCES TO RELATED APPLICATIONS

The present application is a Continuation of PCT/US2010/037268 filed Jun. 3, 2010, which application claims the benefit of U.S. Provisional Application No. 61/183,839 filed Jun. 3, 2009; the full disclosures, each of which are incorporated herein by reference in their entirety.

BACKGROUND OF THE INVENTION

1. Field of the Invention

The invention relates to structures, systems, and methods for treatment of an eye. Exemplary embodiments provide ocular inserts used for drug delivery, along with methods for using ocular inserts positioned on or near the anterior segment of the eye. The exemplary inserts may be worn along the front surface of the eye outside the optical zone, and can deliver one or more drugs at a safe, therapeutically-effective level for at least thirty days.

2. Background of the Invention

A variety of ophthalmic and non-ophthalmic conditions necessitate administration of various drugs to the eye. Eye drops and gels can be effective drug delivery vehicles, but can also have significant disadvantages. Specifically, eye drops mix with fluid in the tear film, but may have a residence time of only 2-5 minutes in the tear film. As little as 5% of the drug may be absorbed locally; some or all of the rest being carried from the lacrimal sac into the lacrimal duct and eventually absorbed into the bloodstream. The absorption into the bloodstream can have at least two adverse effects: first, most of the drug is wasted and, second, the presence of the drug in the bloodstream may have harmful side effects on the rest of the body. Gels may adhere more effectively to the eye, but can also blur the patient's vision for prolonged time periods. Both eye drops and gels need to be reapplied frequently for some therapies. Thus, a need remains for an improved drug delivery method to the eye that is neither cleared out of its targeted location, nor needs frequent reapplication.

In light of the disadvantages of eye drops, it is understandable that a variety of alternatives have been proposed. Among the known alternatives to drops include treatments in which structures containing or impregnated with drugs have been placed under the eyelid.

Such solid ocular dosage forms appear to present significant potential advantages over drop-administered drug treatments of the eyes. In particular, eye drug delivery implants might help overcome low patient compliance, the difficult application and frequent misapplication of traditional eye drops and other dosage forms, and limited effective drug absorption presented by eye drops, while potentially facilitating the advantageous application of advances in polymer chemistry and introduction of the concepts of sustained/controlled drug release from other known drug-delivery systems.

Despite the tremendous potential advantages of drug delivery implants, drug application to the front of the eyes remains dominated by eye drops. Factors that may have contributed to the limited acceptance of prior ocular inserts include their lack of comfort, their propensity for displacement or movement around the eye, their excessive incidents of inadvertent expulsion during sleep or rubbing of eyes, their interference with vision, and/or the difficulty in placing and removing the known drug delivery implants.

In light of the above, new drug delivery devices, systems, and methods would be beneficial, particularly for delivering therapeutic compounds to the anterior segment of the eye. It would be particularly advantageous to provide improved ocular inserts so as to gain both physician and user acceptance, with such inserts ideally being easy to insert and remove, providing patient comfort, being non-toxic and not interfering with vision or oxygen penetration, allowing for reproducible release kinetics, and/or being easy to manufacture at a reasonable price.

BRIEF SUMMARY OF THE INVENTION

The present invention provides therapeutic systems and methods of delivery of at least one drug. Exemplary embodiment delivers one or more drugs from an ocular insert to an anterior portion of an eye, with the insert.

In a first aspect, embodiments of the present invention provide a therapeutic system. The therapeutic system comprises an ocular insert. The ocular insert is placed on a region outside an optical zone of an eye. The ocular insert comprises two structures: a first skeletal structure and a second cushioning structure.

The first structure functions as a skeletal frame which maintains positioning of the implant along the anterior portion of the eye and provides support to the second, cushioning structure. This first structure maintains the attachment of the therapeutic system to the anterior portion of the eye for at least thirty days. In some embodiments the first structure remains a constant size and shape, e.g. a ring shape, a ring with haptics, or a curvilinear ring that is confined to and restrainingly engages the inferior and superior conjunctival fornices so as to retain the implant within the tear fluid and/or against the tissues of the eye.

In many embodiments, the first structure stretches or changes shape so as to maximize its attachment to the anterior structure of the eye. The drug may be dispersed in or on the first structure, on or in the second structure, or both.

In exemplary embodiments of the invention, the therapeutic system is designed for easy insertion and removal by the patient.

BRIEF DESCRIPTION OF THE DRAWINGS

FIG. 2-1 shows an exemplary embodiment of a therapeutic system comprising an ocular insert, that may also include an insertion device, a configuration altering material that dissolves (or swells, weakens, tightens, or effects some other activation mechanism) to reconfigure the implant from an insertion configuration to a deployed configuration, or the like;

FIGS. 2-2 and 2-3 show a top view and cross-sectional view of the therapeutic system shown in FIG. 2-1;

FIG. 2-4 shows an embodiment of the therapeutic system where the ring comprises two radially outwardly and/or anteriorly extending protrusions or bumps on opposed portions of its surface;

FIG. 2-5 shows an alternative embodiment of the ring-shaped therapeutic device system. In this embodiment, a crescent or banana-shaped reservoir is attached to the inferior portion of the ocular insert;

FIGS. 3-1 to 3-3 show another embodiment of the therapeutic system including a ring-shaped structure with a diameter of at least 8 mm, sized to fit outside the optical zone of the cornea, and also having two or more haptics;

FIGS. 4-1 to 4-2 show an alternate embodiment of the therapeutic system in which two or more concentric ring-shaped structures are held together by four or more haptics;

FIG. 4-3 shows an embodiment that employs an eccentric design such that the one or more ring portions or arc segments are present in the inferior area of the ring to target delivery to the area of the eye where tears may more readily pool, as in the cul-de-sac;

FIGS. 5-1 through 5-3 show a serpentine embodiment of therapeutic system which shows an expandable ocular insert;

FIGS. 6-1 and 6-2 show another embodiment where the second cushioning structure comprises two hydrogel scleral contact lenses attached to each other, so as to sandwich the first rigid structure between them;

FIGS. 7-1 shows a close-up of an exemplary ocular insert of the therapeutic device system in which the second structure is disposed throughout the circumferential length of the first structure;

FIG. 7-2 shows a cross-section of a therapeutic device system comprising a second structure with a tapered outer and/or inner edge;

FIG. 7-3 shows a cross-section of a therapeutic device system comprising a second structure with a beveled edge;

FIG. 7-4 shows a cross-section of a therapeutic device system comprising a second structure with a rounded edge;

FIG. 8-1 shows a therapeutic device system with a second structure that may have an anterior and/or posterior surface that can be shaped as well to the radius of curvature of the eye;

FIG. 9-1 shows the second, cushioning structure disposed over discrete portions of the length of the first supporting structure;

FIGS. 10-1 and 10-2 show an embodiment where the coating is partially dispersed around the second structure to allow for preferential expansion of the second structure in certain areas;

FIG. 11-1 shows a ring-shaped ocular insert in which separated and/or opposed portions are approximate or pinched in toward the center to form a non-planar taco shape;

FIG. 11-2 shows the ring-shaped ocular insert upon insertion on the surface of the eye, before a dissolvable material has allowed for a slow release back into a ring-shape;

FIGS. 11-3 and 11-4 show an embodiment where the annular shape includes a serpenting shape or series of bends such that radially outer portions or protrusions are interspersed with radially inner portions;

FIGS. 11-5 and 11-6 show an alternative embodiment 88 where a three-leaf clover shape is produced;

FIG. 11-7 shows a fully expanded ocular insert positioned on the surface of the eye;

FIGS. 12-1 and 12-2 show two alternatives of a modified grasping tool, with a notch or groove on the end to facilitate grasping the device;

FIGS. 12-3 to 12-6 show different embodiments for jaws of the grasping tool modified to have a specific shape on the notch to help fold the device into a shape that matches that of the eye and a method of using it;

FIGS. 13-1 to 13-4 show an alternative manner of releasing the ring from the grasping tool;

FIGS. 14-1 to 14-5 show an alternative syringe-shaped insertion device, along with a method for, inserting the ring-shaped ocular insert;

FIGS. 15-1 to 15-3 show another alternative ocular insert insertion device that resembles a classical bike horn;

FIGS. 16-1 to 16-6 show an alternative insertion device comprising a soft flexible cone that supports the ring-shaped device along its outer rim and a method of using it to place an ocular insert on the sclera of the eye; and FIGS. 17-1 to 17-2 show an alternative insertion device comprising a flexible curved band.

DETAILED DESCRIPTION OF THE INVENTION AND PREFERRED EMBODIMENTS

Figure 1:
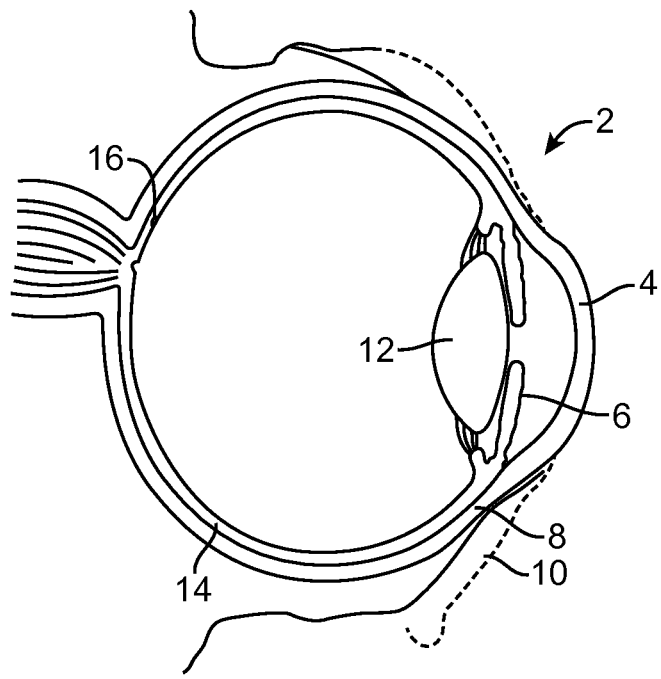
FIGS. 1-1 and 1-2 show an anatomical tissue structure of an eye 2 suitable for treatment with ocular inserts.
Figures 1, 2:
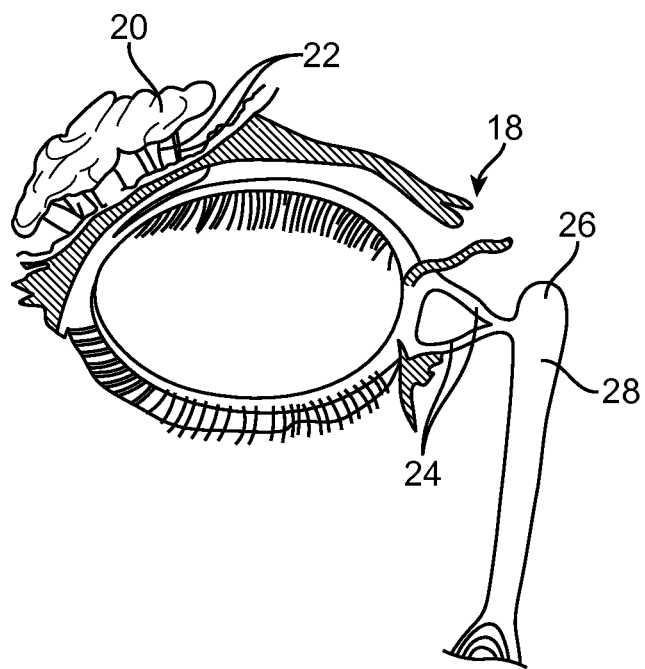

FIGS. 1-1 and 1-2 show an anatomical tissue structure of an eye 2 suitable for treatment with ocular inserts. The eye 2 includes a cornea 4, an iris 6, and a white-colored sclera 8. A substantially transparent conjunctival layer 10 covers the sclera 8. Posterior to the cornea 4 lies a crystalline lens 12. A retina 14 that responds to light is located in the posterior portion of the eye. A fovea 16 is a part of the retina that provides sharp focused vision. The cornea 4 and lens 12 refract light to form an image on the fovea 16 and retina 14.

FIG. 1-2 shows the lacrimal system 18 which is responsible for producing and draining the tear fluid. The lacrimal system consists of two general areas: first, the lacrimal gland 20, which secretes the tears, and its excretory ducts 22, which transport the fluid to the surface of the eye and, second, the lacrimal canaliculi 24, the lacrimal sac 26, and the nasolacrimal duct 28, which bring the tear fluid is conveyed into the nose cavity.

FIG. 2-1 shows an exemplary embodiment of a therapeutic system 30. The therapeutic system 30 comprises an ocular insert 31, and may also include an insertion device, a configuration altering material that dissolves (or swells, weakens, tightens, or effects some other activation mechanism) to reconfigure the implant from an insertion configuration to a deployed configuration, or the like. In alternative embodiments, activation of the insertion device (or some other tool) may also reconfigure the insert from the insertion configuration to the deployed configuration, or may simply releasably hold the insert in a manner so as to assist insertion. In still further embodiments, the ocular insert may not undergo significant changes in shape or other properties before, during, or after deployment. Regardless, the ocular insert is eventually positioned on a region outside an optical zone of an eye. The ocular insert comprises two structures: a first structure 32 and a second structure 34. FIG. 2-1 shows the exemplary therapeutic system 30 placed outside the optical zone of the eye.

First Structure

The first structure functions as a skeleton which largely holds the implant in place relative to the structures of the eye, thereby attaches the implant to the eye, and thus provides support for the cushioning structure relative to the anterior portion of the eye. This first or skeletal structure preferably maintains the attachment of the therapeutic system to the anterior portion of the eye for at least thirty days. Should it become medically desirable or should a patient so desire, the therapeutic system may be removed sooner than the thirty days; however, from a physical standpoint, it is capable of maintaining the ocular insert of the anterior surface of the eye for at least thirty days. In some embodiments, the first structure may continue to help maintain the overall implant in the eye for sixty days or more, for ninety days or more, or even for 180 days or more, ideally with safe and effective delivery of therapeutic agents continuing throughout such implant periods. Alternative treatment devices and methods may benefit from shorter implant periods, optionally for periods of one or more days, at least a plurality of days, a week or more, two weeks or more, or the like.

Due to its role as skeleton for the insert 31 of therapeutic system 30, the first structure may determine the overall shape of the ocular insert. The first structure typically comprises a thin metal wire, a hard plastic such as nylon, PMMA, polycarbonate, polyethylene terepthalate, and/or another polymer, polypropylene or other synthetic suture material capable of providing the structural support to maintain the therapeutic system attached to the eye. The first structure may also comprise a coated plastic or metal such that the coating contains the therapeutic medication or provides easier attachment of the second, cushioning element to the skeletal member. The first structure may have a surface treatment such as plasma etching or the like to enable the second structure to be suitably attached to the skeletal member.

Figures 1, 2:
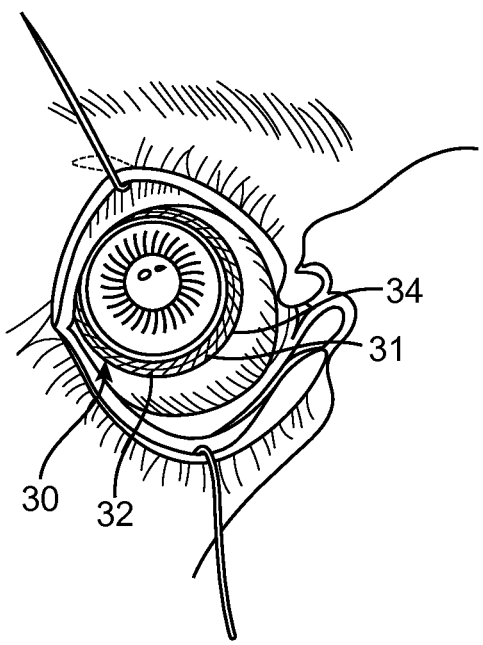
Figure 2:
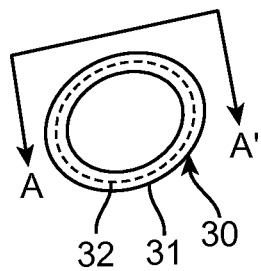
Figures 2, 3:
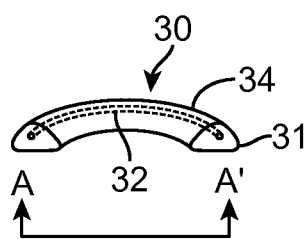

FIG. 2-1 shows a basic embodiment of the first structure. Here the first structure 32 is annular or ring-shaped and, has a diameter of at least 8 mm, and is sized to fit outside the optical zone of the cornea so as not to interfere with patient vision. The annulus of first structure 32 will preferably comprise a complete ring or torroid, but may have some gap along its circumference. The arc angle of the annulus in such embodiments will be over 180°. FIGS. 2-2 and 2-3 show a top view and cross-sectional view of the therapeutic system shown in FIG. 2-1. The therapeutic system shown in FIGS. 2-1 to 2-3 can be sized much larger so that the edges of the structure will lie within the cul-de-sac of the eye. In the case where the therapeutic system is intended to be located within the cul-de-sac of the eye, the therapeutic system will desirably be produced in at least two sizes to accommodate varying sizes of eyes (e.g. pediatric versus adult, and optionally different adult eye sizes). Alternative shapes of the first structure may include those of the inserts shown and described in U.S. Pat. No. 3,995,635, the disclosure of which is incorporated herein by reference.

Figures 2, 3, 4:
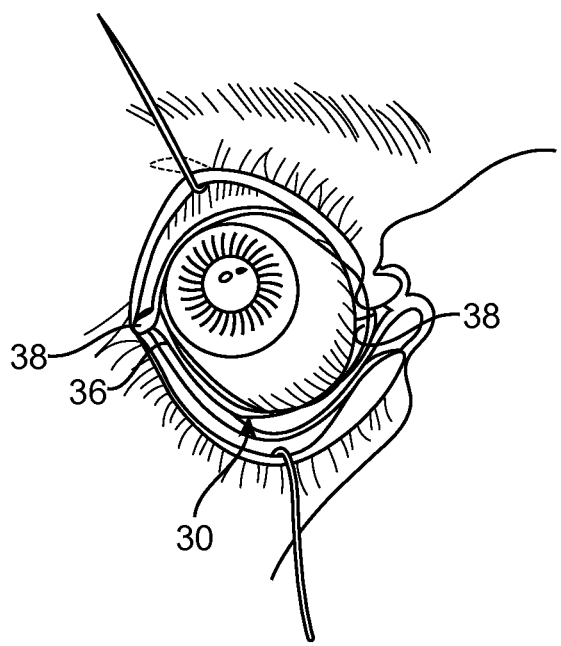

FIG. 2-4 shows an embodiment 36 of the therapeutic system 30 where the ring comprises two radially outwardly and/or anteriorly extending protrusions or bumps 42 on opposed portions of its surface. When the eye blinks, the lids "trap" the two bumps between the lids and push the ocular implant (which otherwise can freely glide on the surface of the eye) back into its therapeutically effective position outside the optical zone of the cornea.

FIG. 2-5 shows an alternative embodiment 40 of the ring-shaped therapeutic device system 30. In this embodiment, a crescent or banana-shaped reservoir 42 is attached to the inferior portion of the ocular insert.

FIGS. 3-1 to 3-3 show another embodiment 44 of the therapeutic system 30 again including a ring-shaped structure with a diameter of at least 8 mm, sized to fit outside the optical zone of the cornea, and also having two or more haptics 46, each radiating from the ring-shaped structure across to the cul-de-sac of the eye, thus providing an additional support point for the therapeutic system. FIG. 3-1 shows the ring-shaped therapeutic system with haptics placed on the anterior structure of the eye. FIGS. 3-2 and 3-3 show a top- and a cross-sectional view, respectively, of ocular insert 44.

FIGS. 4-1 to 4-2 show an alternate embodiment 48 of the therapeutic system 30 in which two or more concentric ring-shaped structures 52 are held together by four or more haptics 50. The inner ring-shaped structure has a diameter of at least 8 mm and is sized to fit outside the optical zone of the cornea. The next (and subsequent) outer ring-shaped structures have progressively larger diameters, the outermost ring-shaped structure optionally having a diameter of at least 12 mm and being sized to fit on the sclera, fornix or cul-de-sac of the eye. FIG. 4-1 shows the embodiment 48 of the therapeutic system placed on the eye. FIG. 4-2 shows the embodiment 48 of the therapeutic system before insertion on the eye. The embodiment 48 has the advantage of providing a larger surface area for drug delivery, due to the presence of the two or more rings and four or more haptics. Additional insert shapes having enhanced surface areas may be seen in U.S. Pat. No. 4,540,417, the disclosure of which is incorporated by reference. FIG. 4-3 shows a related embodiment 49 that employs an eccentric design such that the one or more ring portions or arc segments 54 are present in the inferior area of the ring to target delivery to the area of the eye where tears may more readily pool, as in the cul-de-sac. This eccentric design may also stabilize the device in a more fixed position and be less likely to rotate out of position or move into the optical zone of the eye. In addition, targeting delivery to the cul-de-sac may enable more effective delivery of some medications to the nasolacrimal system in addition to the ocular surface, such as in the case of nasal allergy medications.

In the embodiments described above, the first structure typically remains of a constant size and shape, e.g. a ring-shape, or a ring with haptics that anchor/attach to the sclera, fornix or cul-de-sac of the eye.

Figures 2, 3, 4, 5:
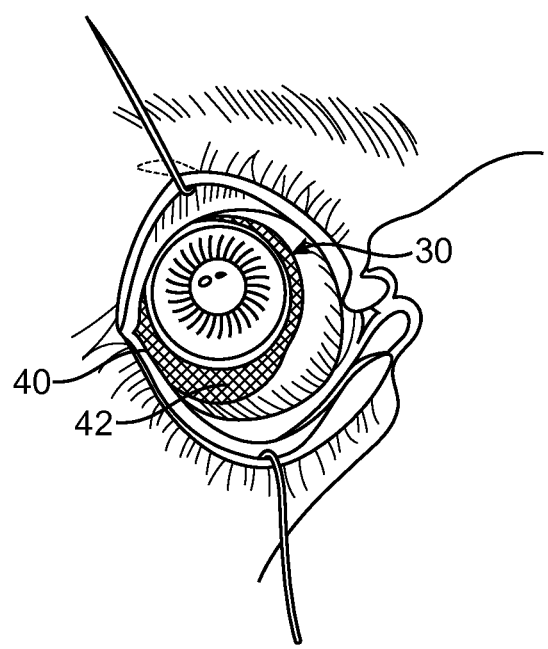
Figures 1, 3:
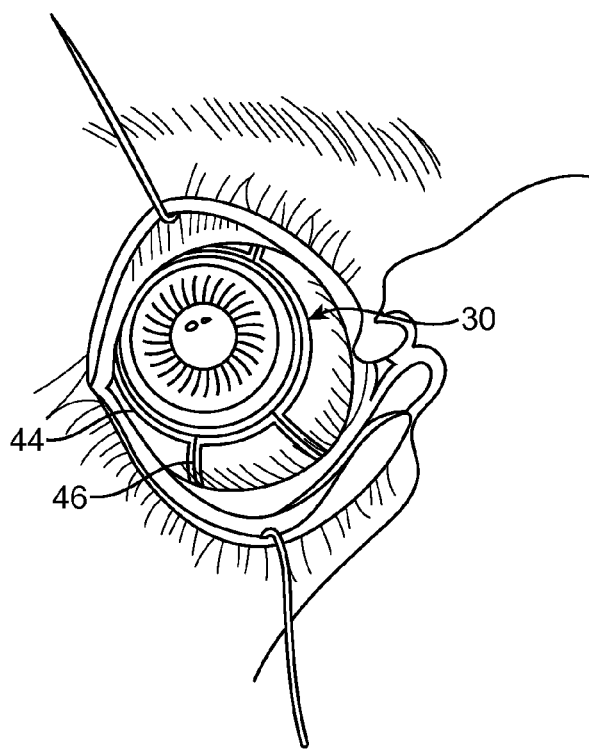
Figures 2, 3:
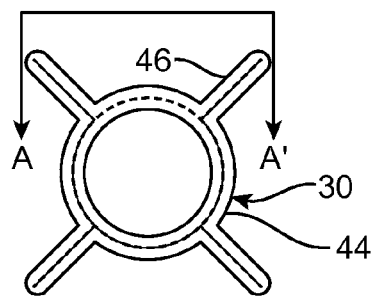
Figure 3:
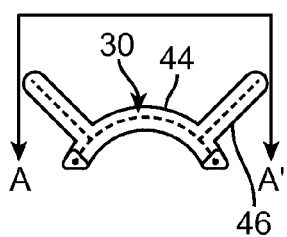
Figures 1, 4:
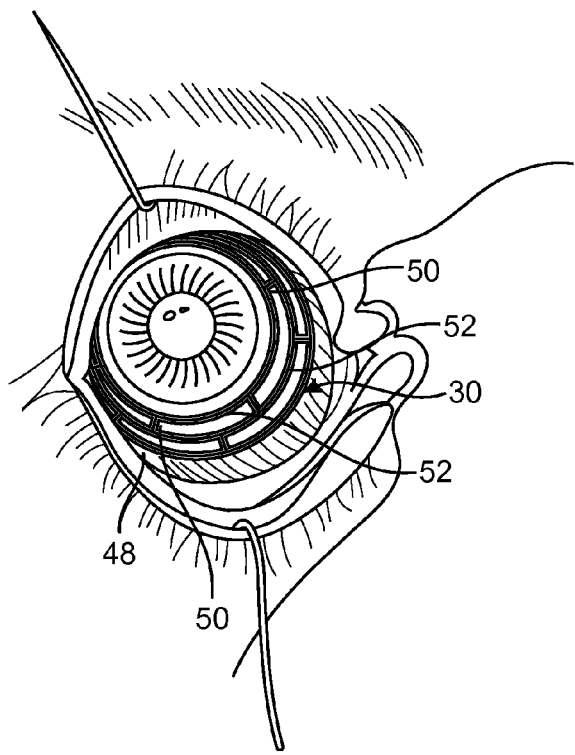
Figures 2, 4:
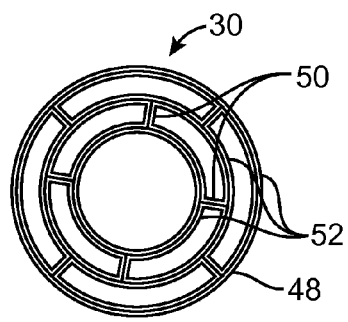
Figures 3, 4:
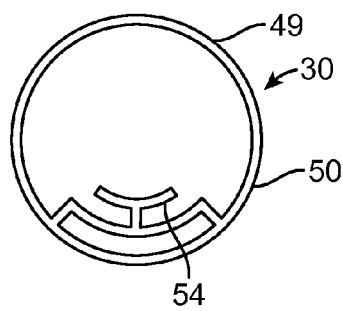
Figures 1, 5:
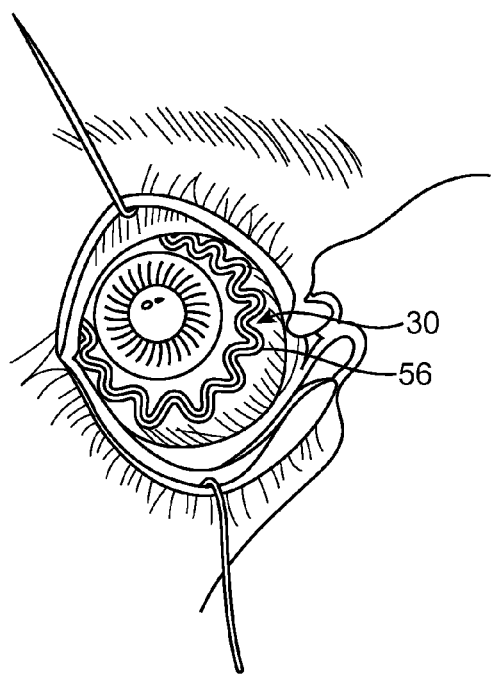
Figures 2, 5:
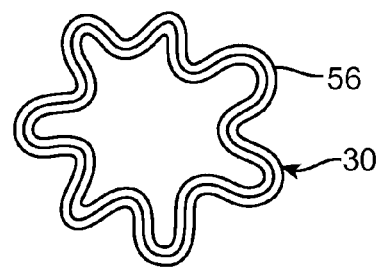
Figures 3, 5:
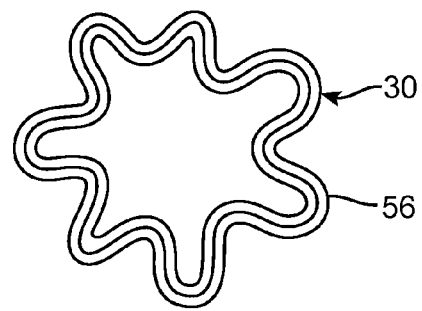

In other embodiments, the first structure can expand or change shape so as to enhance its attachment to the anterior structure of the eye. FIGS. 5-1 through 5-3 show a serpentine embodiment 56 of therapeutic system 30 which shows an expandable ocular insert. FIG. 5-1 shows the embodiment 56 inserted on the surface of the eye; FIG. 5-2 shows the embodiment 56 before insertion, and FIG. 5-3 shows the embodiment in its expanded state. A variety of alternative serpentine configurations may be developed or modified so as to take advantage of the cushioning and/or configuration-changing techniques described herein, including those of U.S. Pat. No. 4,540,417, the disclosure of which is incorporated herein by reference.

With respect to the already described embodiments, the skeletal member can be shaped to conform to the radius of curvature of the eye.

The first structure can expand as it absorbs fluid from the tear fluid in the eye or can stretch through a spring action mechanism. Examples of materials that can swell upon insertion in the eye include PVPE, PVA and polyurethane gels. Examples of materials that may stretch through spring action include platinum alloys, titanium alloys, all stainless steel alloys & tempers, various clad metals and insulated wires. The first structure may comprise a shape-memory material, such as nitinol, which will allow it to change to a desired shape using thermal, magnetic or electromagnetic activation, from a martensitic to an austenitic state. Other examples of shape memory materials include shape memory polyurethanes, crosslinked trans-polyoctylene rubber, polynorbornene polymers, nitinol, polyethylene, PMMA, polyurethane, cross-linked polyethylene, cross-linked polyisoprene, polycycloocetene, polycaprolactone, copolymers of (oligo) caprolactone, PLLA, PL/DLA copolymers, PLLA PGA copolymers, and other shape memory materials well-known to those of ordinary skill in the art.

Additional Configurations of the First Structure

Figures 1, 6:
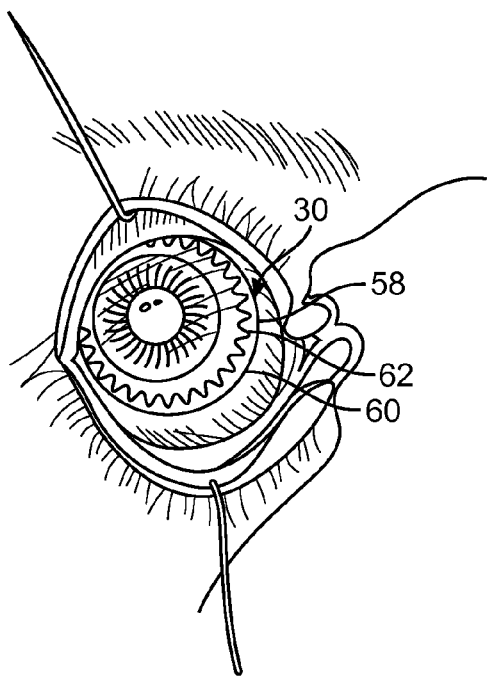
Figures 2, 6:
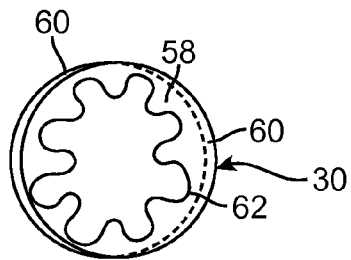

FIGS. 6-1 and 6-2 show another embodiment 58 where the second cushioning structure comprises two hydrogel scleral contact lenses 60 attached to each other, so as to sandwich the first rigid structure between them. FIG. 6-1 shows the embodiment 58 placed on the surface of the eye; FIG. 6-2 shows the embodiment 58 before placement. In embodiment 58, the first structure 62 functions as a skeleton for the ocular insert and serves as a drug delivery material. As tear fluid penetrates the hydrogel lenses, it comes into contact with the first structure and causes the drug to elute into the tear fluid. Another embodiment (not shown) comprises an exoskeletal first structure comprising a drug delivery material attached to the anterior side of a contact lens. Another embodiment (also not shown) comprises a first structure comprising a drug delivery material placed on an eye and covered by a regular, non-drug delivery contact lens to provide a comfortable lid movement.

Second Structure

Figures 1, 7:
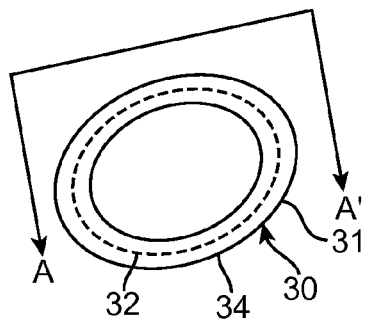
Figures 2, 7:
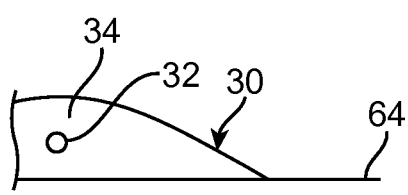
Figures 3, 7:
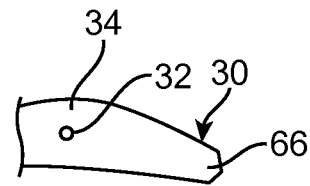
Figures 4, 7:
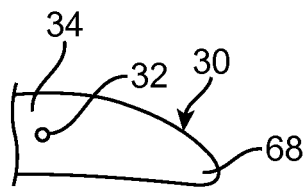

FIGS. 7-1 shows a close-up of an exemplary ocular insert 31 of the therapeutic device system 30 in which the second structure 34 is disposed throughout the circumferential length of the first structure 32. The second structure 34 provides cushioning to facilitate extended implantation or wearing of the device, optionally inhibiting irritation to the eye sufficiently to encourage a patient to wear the therapeutic system for at least thirty days. The cushioning effect may be achieved at least in part by the material used in the second structure, as well as by the shape of the surfaces and/or edges of the second structure. In some embodiments, the second structure may comprise a coating.

Desirably the material of the second structure is soft, biocompatible, and non-irritant. Examples of such material comprise polymers such as hydrogel or silicone.

Figures 1, 8:
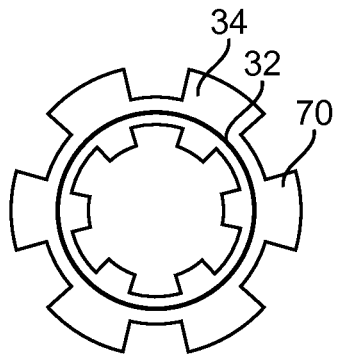

Regardless of its overall shape and configuration, edges of the second structure are often shaped so as to inhibit friction between them and the inside portion of the eyelid. FIG. 7-2 shows a cross-section of a therapeutic device system comprising a second structure 34 with a tapered outer and/or inner edge 64. FIG. 7-3 shows a cross-section of a therapeutic device system comprising a second structure 34 with a beveled edge 66. FIG. 7-4 shows a cross-section of a therapeutic device system comprising a second structure 34 with a rounded edge 68. FIG. 8-1 shows a therapeutic device system 30 with a second structure 34 that may have an anterior and/or posterior surface 70 that can be shaped as well to the radius of curvature of the eye 70.

Figures 1, 9:
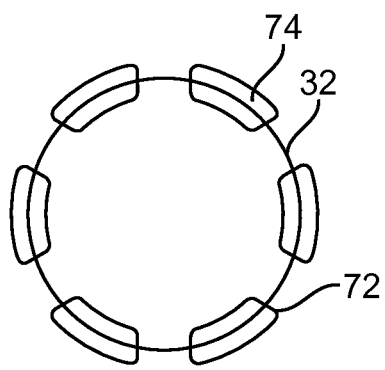

In some embodiments 72 the second, cushioning structure 74 is disposed only over certain discrete portions along the length of the first structure, desirably at locations where sharper edges or bends may provoke irritation to the eye. FIG. 9-1 shows the second, cushioning structure 74 disposed over discrete portions of the length of the first supporting structure 32.

Figures 1, 10:
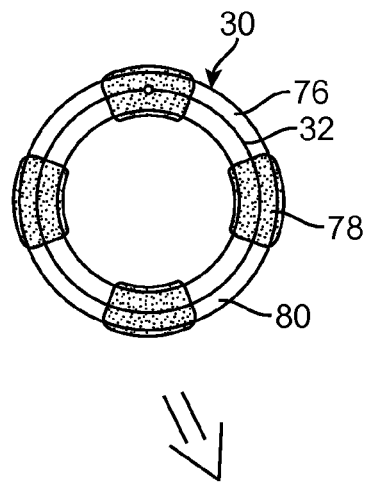
Figures 2, 10:
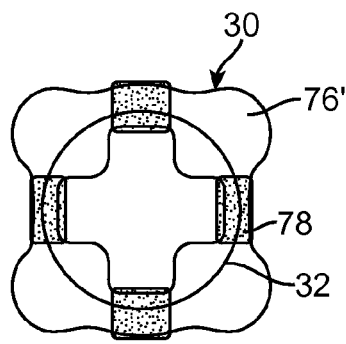

The second structure may also comprise a coating, partially disposed on the second structure, which prevents the expansion of the otherwise expandable, desirably hydratable, second structure. FIGS. 10-1 and 10-2 show an embodiment 76 where the coating 78 is partially dispersed around the second structure to allow for preferential expansion of the second structure in certain areas. FIG. 10-1 shows an embodiment where the coating is partially dispersed around the second structure 80, with the first structure 32 in an unhydrated state. FIG. 10-2 shows the embodiment of the second structure 80 of FIG. 10-1 in a hydrated, thus expanded, state 76'.

In one embodiment, the first and second structure may comprise similar compositions or materials having differing durometers and/or other characteristics, particularly where the material can be processed so as to exhibit the desired properties for both the first and second structures.

Drug Delivery Matrix

The drug used in the therapeutic system will often be placed on, embedded, encapsulated or otherwise incorporated into a delivery matrix. The delivery matrix may be included in or on either the first skeletal structure or the second cushioning structure, or both. The delivery matrix, in turn, comprises either a biodegradable or a non-biodegradable material. The delivery matrix may include, although it is not limited to, a polymer. Examples of biodegradable polymers include protein, hydrogel, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid), and combinations thereof. Non-biodegradable polymers may comprise silicone, acrylates, polyethylenes, polyurethane, polyurethane, hydrogel, polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY® from Elgin Specialty Metals, Elgin, Ill.; CONICHROME® from Carpenter Metals Corp., Wyomissing, Pa.).

To prevent a potential allergic reaction to the ocular insert in a patient, the ocular insert, desirably will comprise a hypoallergenic, material. Desirably, either or both the first and /or second structure may comprise materials such as hydrogels, polyethylene glycol (PEG), or polyethylene oxide (PEO) that prevent adhesion of proteins and thus minimize the chance of developing an allergic reaction. Alternatively, the drug delivery matrix of the ocular insert may comprise an anti-allergenic and/or antihistaminic compound to prevent an allergic reaction to the ocular insert. In certain embodiments, the delivery matrix may also include other materials known in the art.

Therapeutic System Drugs

A variety of drugs may be delivered to the eye using the therapeutic system. Desirably these drugs will include drugs needed for long-term treatment to the eye. Examples of conditions that require long-term treatment include: dry eye, glaucoma, allergies, infections, bacterial, viral and other infections, chronic inflammatory conditions such as acne rosacea keratitis, cyclitis, and blepharitis, selected retinal conditions such as diabetic retinopathy, age related macular degeneration and other retinal conditions, post-surgery, amblyopia, etc.

Some drug families used in the treatment of the above-mentioned conditions comprise: steroids, anti-inflammatories, antibiotics, glaucoma treatment compounds, antihistamines, dry eye medication, neuroprotectives, retinoids, antineovasculars, antioxidants, and biologics.

Examples of steroids include glucocorticoids, aprogestins, amineralocorticoids, or corticosteroids. Exemplary corticosteroids include cortisone, hydrocortisone, prednisone, prednisolone, methylprednisone, triamcinolone, fluorometha-lone, dexamethasone, medrysone, betamethasone, loteprednol, fluocinolone, flumethasone, rimexolone or mometasone. Other examples of steroids include androgens, such as testosterone, methyltestosterone, or danazol.

Examples of anti-inflamatories include NSAIDs such as piroxicam, aspirin, salsalate (Amigesic), diflunisal (Dolobid), ibuprofen (Motrin), ketoprofen (Orudis), nabumetone (Relafen), piroxicam (Feldene), naproxen (Aleve, Naprosyn), diclofenac (Voltaren), indomethacin (Indocin), sulindac (Clinoril), tolmetin (Tolectin), etodolac (Lodine), ketorolac (Toradol), oxaprozin (Daypro), and celecoxib (Celebrex).

Examples of antibiotics include amoxicillin, penicillin, sulfa drugs, erythromycin, streptomycin, tetracycline, clarithromycin, terconazole, azithromycin, bacitracin, ciprofloxacin, evofloxacin, ofloxacin, levofloxacin, moxifloxacin, gatifloxacin, aminoglycosides, tobramycin, gentamicin, as well as polymyxin B combinations including polymyxin B/trimethoprim, polymyxin B/bacitracin, polymyxin B/neomycin/ gramicidin.

Glaucoma treatment medications include beta-blockers, such as timolol, betaxolol, levobetaxolol, and carteolol; miotics, such as pilocarpine; carbonic anhydrase inhibitors, such as brinzolamide and dorzolamide; prostaglandins, such as travoprost, bimatoprost, and latanoprost; seretonergics; muscarinics; dopaminergic agonists; and adrenergic agonists, such as apraclonidine and brimonidine, and prostaglandins or prostaglandin analogs such as latanoprost, bimatoprost, or travoprost.

Antihistamines and mast cell stabilizers include Olopatadine and epinastine, the acute care anti-allergenic products ketorolac tromethamine, ketotifen fumarate, loteprednol, epinastine HCl, emedastine difumarate, azelastine hydrochloride, Olopatadine hydrochloride, ketotifen fumarate; while the chronic care anti-allergenic products include pemirolast potassium, nedocromil sodium, lodoxamide tromethamine, cromolyn sodium.

Antineovasculars include biologics, Ranibizumab (Lucentis) and Bevacizumab (Avastin). Amblyopia medicine includes anesthetics and cycloplegics such as atropine. Dry eye medication includes cyclosporine.

Control of the Drug Elution Process

Drug elution can be controlled either through concentration of the drug present, or by embedding into or combining the drug with various other compounds. The drug's particular solubility characteristic, whether hydrophobic or hydrophilic, will determine the means of controlling the rate of elution for that particular drug. In some embodiments where the drug is hydrophobic, the drug may be finely ground up and dispersed into the second cushioning structure comprising silicone or a polymer such as hydrogel that is highly hydrophilic. Hydrophilic drugs can either be immobilized in a first structure, e.g. a plastic, or a second structure such as a hydrogel. The specific choice of polymers used for immobilizing depends on the drug and its characteristics, the rate of elution desired, and the wall thickness of the coating that contains the drug which may also alter the rate of elution. For instance, if the drug is embedded in a first polymer, then the wall thickness of the second polymer may at least in part control the rate at which the drug passes through. Conversely, the wall thickness of the coating may be used to control drug release if the drug is embedded into the skeletal element.

Other considerations may include choice of substrate material for the skeleton and whether the drug can be incorporated into the skeleton, then cast into the specific skeletal shape, and then coated with a hydrogel or other polymer.

In the case of hydrophobic drugs, surfactants comprising bile salts (e.g. deoxycholate, taurodeoxycholate, and glycocholate) or calcium chelators, such as ethylenediaminetetraacetic acid (EDTA), may be added to increase their solubility.

Conversely, to decrease the rate of elution, the drug particles may be coated, a less soluble salt form of the drug may be produced, or a rate-limiting coating, polymer, or other material may be incorporated in and/or on the delivery matrix such that the distance the drug travels to exit the device or the resistance of the material to passage of the drug restricts flow of the drug from the device.

Other variables include whether or not the polymer absorbs enough aqueous/tear fluid to force the drug out of the matrix, such as a sponge-like or naturally porous material or a material with artificially created pores or other materials that saturate such that an osmotic pumping effect occurs.

The surface area and geometric configuration of the therapeutic system can also be used to control the elution rate of the drug. The geometric configuration of the therapeutic device can be thus designed to maximize, or minimize, the flow of tear fluid over the therapeutic system, according to the specific need. For example, an increased surface area will increase the contact area between the drug and the tear fluid. The device could also be constructed such that it has more delivery area/surface area in the lower or upper fornix depending on if a targeted delivery is desired. Conversely, to decrease the elution rate of the drug, the contact area between the eye and the drug particles should be decreased.

Therapeutic System Coatings

In some embodiments, the second structure also comprises a coating to further soothe the patient's eye. The coating may comprise a lubricious material, e.g., Hydak® hyaluronan-based coating from Biocoat. The advantages of Hydak include that it is lubricious when wet, biocompatible, highly hydrophilic, may be applied using thin, flexible coatings, and it is a carrier for bioactive substances. Other coatings could also include either hydrophilic or drug delivery coatings from SurModics (hydrophilic or drug delivery) and Hydromer.

To ease the insertion process, some embodiments will be coated so that the ocular inserts will have a firm texture during insertion. Once such ocular inserts are in place, the coating will dissolve to allow the ocular insert to become more comfortable for every-day use.

Insertion and Removal of the Therapeutic System

The therapeutic system may first be placed onto the eye by a physician and then, once a desired drug-delivery time period is complete, subsequently be removed from the anterior surface of the eye by the same or a different physician. The physician may optionally then teach the patient how to insert and then take out the ocular implant by him- or herself A challenge to insertion and removal of the device comes from maintaining the fine balance between rigidity and flexibility. A device that is too flexible will be very difficult to insert; while a device that is too rigid will be uncomfortable to wear for extended periods of time.

One way of maintaining the fine balance between rigidity and flexibility is by folding or pinching the device into various shapes. The folds in the device create a structure that maintains its shape more effectively during insertion and thus is more "pushable" than a ring structure that deforms easier.

One alternative for maintaining the folds in the device for purposes of insertion is to tether the folds with a dissolvable material until the device is placed in the eye. The dissolvable material allows for a slow release of the shape back into a ring.

Figures 1, 11:
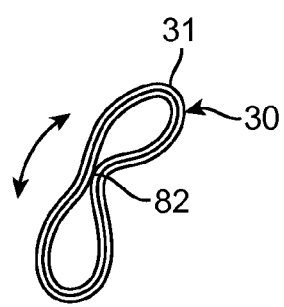
Figures 2, 11:
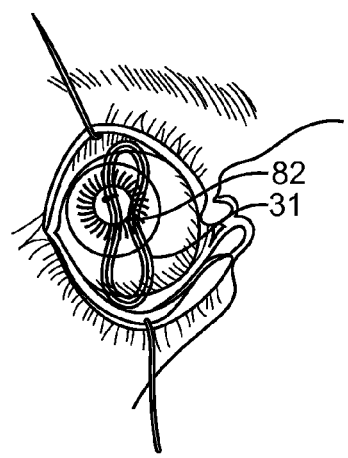
Figures 3, 11:
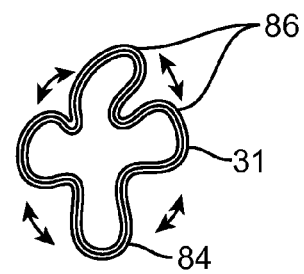
Figures 4, 11:
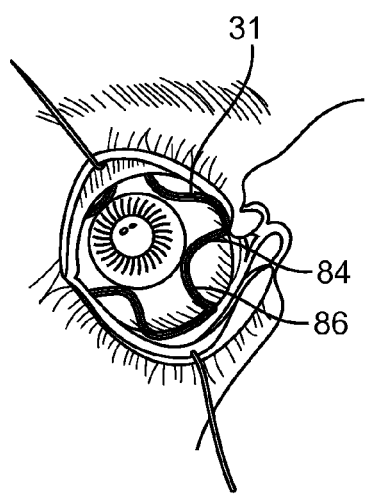
Figures 5, 11:
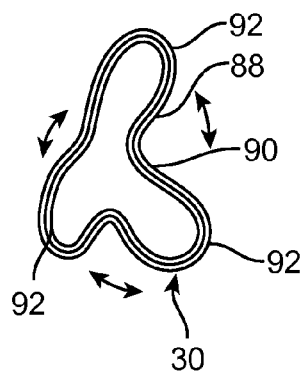
Figures 6, 11:
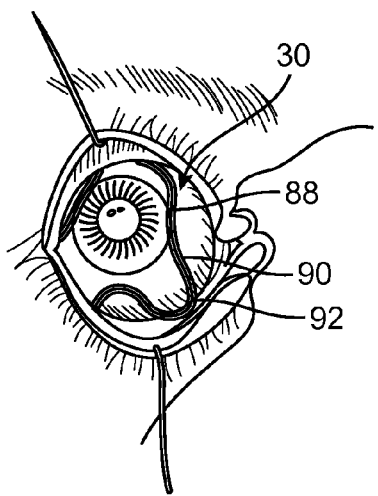
Figures 7, 11:
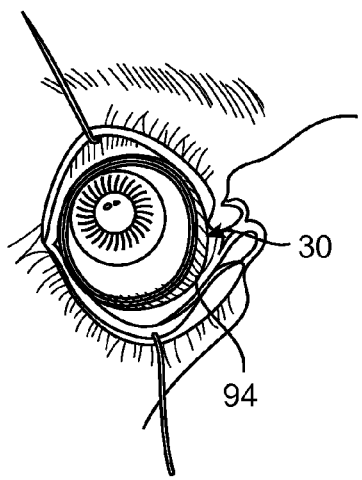

FIG. 11-1 shows a ring-shaped ocular insert 31 in which separated and/or opposed portions are approximate or pinched in toward the center to form a non-planar taco shape 82. The pinched ring-shaped device can be positioned such that one end can be slipped under the lower or upper lid, then the other end can be positioned under the other lid. FIG. 11-2 shows said ocular insert 31 upon insertion on the surface of the eye, before a dissolvable material has allowed for a slow release back into a ring-shape; FIG. 11-7 shows said device on the surface of the eye, in its fully expanded state 94.

FIG. 11-3 shows one embodiment 84 where the annular shape includes a serpenting shape or series of bends such that radially outer portions or protrusions are interspersed with radially inner portions. This embodiment has four protrusions and a clover leaf shape is produced such that each of the four protrusions 86 would facilitate placement into the upper and lower lids as well as the nasal and temporal aspects of the eye. The inner portions of this shape could also be held together (or near each other) with a dissolvable material, but it may not be necessary since a good initial position could be achieved. FIG. 11-4 shows said embodiment 84 upon insertion on the surface of the eye; FIG. 11-7 shows said device on the surface of the eye, in its fully expanded state 94.

FIG. 11-5 shows an alternative embodiment 88 where a three-leaf clover shape 90 is produced. In this case the top protrusion 92 would first be inserted behind the top eyelid and then the bottom two protrusions would be inserted behind the bottom eyelid. As in the previous embodiment, this shape could also be held in place with a dissolvable material, but it may not be necessary since a good initial position could be achieved. FIG. 11-6 shows said device upon insertion on the surface of the eye; FIG. 11-7 shows said device on the surface of the eye, in its fully expanded state 94.

Figures 1, 12:
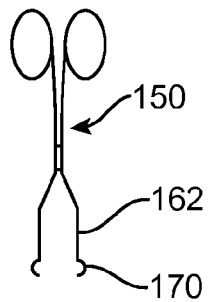
Figures 2, 12:
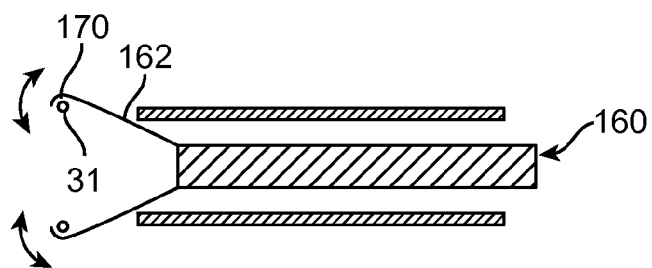
Figures 3, 12:
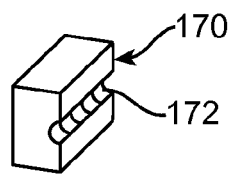
Figures 4, 12:
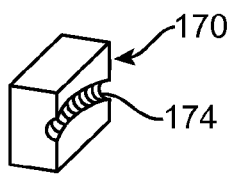
Figures 5, 12:
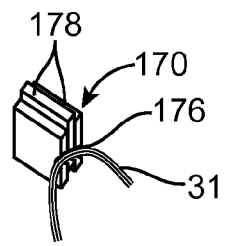
Figures 6, 12:
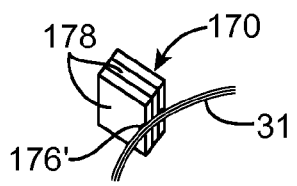

Insertion of the device can also be facilitated by use of delivery instruments. FIGS. 12-1 and 12-2 show two alternatives of a modified grasping tool 150 and 160, with a notch or groove 170 on the end to facilitate grasping the device. Desirably, the jaws have an antramatic distal surface with, for example, a top layer comprising silicone or Teflon so that if they come in contact with the surface of the eye, they will not scratch it. In FIG. 12-2, an embodiment of a delivery instrument that can accommodate two or more jaws is shown, there are preferably three or four jaws 162 (the drawing shows two jaws for simplicity) that create the three or four leaf clover shape when the device 160 is clamped onto the ring. The three or four jaws 162 come together simultaneously via an outer tube that forces the tines of the jaws to compress from their more relaxed outward position.

FIGS. 12-3 to 12-5 show different embodiments for jaws 162 of the grasping tool modified to have a specific shape on the notch to help fold the device into a shape that matches that of the eye. FIG. 12-3 shows jaws with a groove 172 that runs horizontally across the jaws. FIG. 12-4 shows jaws with a groove 175 that is curved so as to bend the ring into a shape that conforms more easily to the shape of the eye.

FIG. 12-5 shows an alternative antramatic embodiment of a jaw with a curved groove 176. In this embodiment the jaw consists of three adjacent slabs with a horizontal groove. As shown in FIG. 12-5, to grab the ring-shaped ocular insert 31, the middle slab 178 is raised slightly, to allow the formation of a curved groove for the ring material. As shown in FIG. 12-6, to release the ocular insert 31, once the protruding fold of the ring has touched the surface of the eye, the middle slab is pushed down so that all the slabs are flush with each other and the groove running on the side of the three slabs is now horizontal; the ring will now be easily released from the grasping tool.

FIGS. 13-1 to 13-4 show an alternative manner of releasing the ring from the grasping tool. FIG. 13-1 shows a modified grasping tool 160 comprising four jaws 162, each jaw comprising a groove 170 positioned at the anterior end of each jaw and facing the center of the grasping tool. FIG. 13-2 shows a modified grasping tool 160 that has grasped an ocular insert 31 in the grooves 170, tightened the jaws 162 on the insert, creating four protrusions to ease insertion of the ocular insert behind a patient's eye lids. Once the protruding folds of the ring-shaped device have been placed on the eye, the arms with the jaws each turn 180° so that the groove is not located along the external circumference of the gasping tool; the folded ring can now slide out easily, as it is no longer maintained in the groove. FIG. 13-3 shows the modified grasping tool 160 where each jaw has turned approximately 180° so that each groove 170 now faces away from the center of the grasping tool. The 180° turn of the grooves has resulted in a release of the ocular insert 31. FIG. 13-4 shows the ocular insert 131 released from the modified grasping tool 160.

Figures 1, 14:
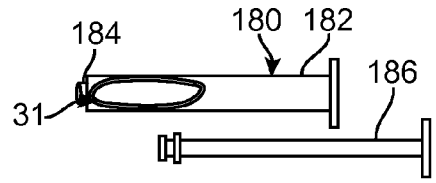
Figures 2, 14:
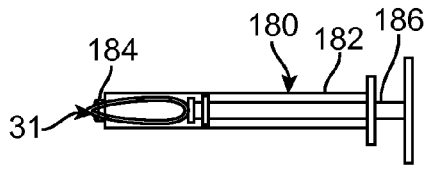
Figures 3, 14:
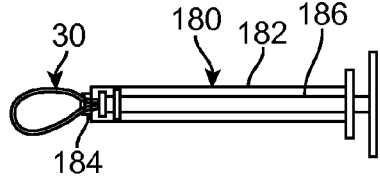
Figures 4, 14:
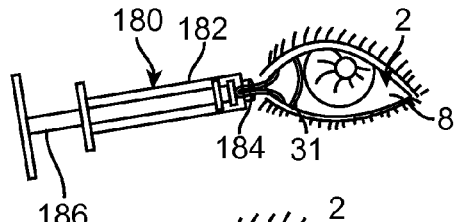
Figures 5, 14:
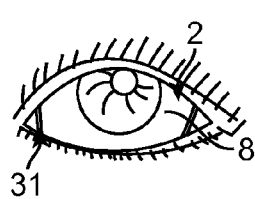

FIGS. 14-1 to 14-5 show an alternative device, along with a method for, inserting the ring-shaped device. FIG. 14-1 shows a syringe-shaped device 180 comprising a barrel 182 with a flat tip 184 through which ocular insert 31 can be pushed, and a plunger 186. To insert the ring-shaped device in the syringe, the plunger of the syringe is taken out, the ring-shaped device is folded flat and inserted into the body of the syringe and the plunger is placed back into the syringe. FIG. 14-2 shows a syringe-shaped device 180 where and ocular insert 31 has been folded flat and inserted into the barrel 182. The plunger 186 has been inserted into the barrel, with the barrel comprising a lumen and the open tip comprising a port through which insert 31 can be pushed. To insert the ring-shaped device into the eye, the plunger pushed into the body of the syringe so as to allow the ring-shaped device to slowly squeeze through the flat tip of the syringe. FIG. 14-3 shows the loop of the ocular insert 31 substantially extruded from the tip 184 of the syringe-shaped device 180 and ready for placement on the sclera of the eye. FIG. 14-4 shows the loop of the ocular insert 31 partially placed on the sclera of the eye; the rest of the ocular insert will be pushed through the tip 184 of the syringe-shaped device 180 and released onto the eye. FIG. 14-5 shows the ocular insert 31 placed on the sclera of the eye.

Figures 1, 15:
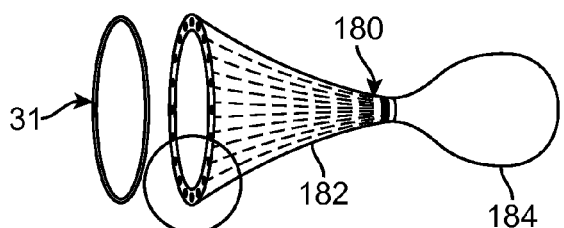
Figures 2, 15:
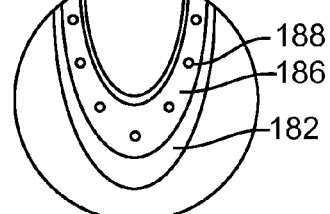
Figures 3, 15:
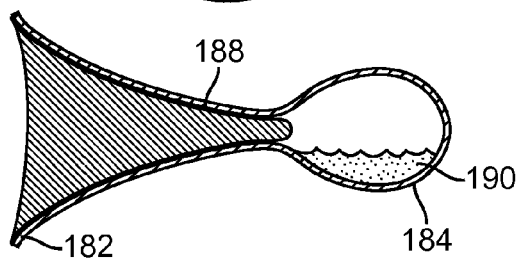

FIGS. 15-1 to 15-3 show another alternative ocular insert insertion device that resembles a classical bike horn. FIG. 15-1 shows a bike horn-shaped insertion device 180 comprising two parts: a trumpet 182 and a squeeze bulb 184. FIG. 15-2 shows a close-up of the trumpet 182. The trumpet comprises a soft material 182 with channels 188 that connect the squeeze bulb to the outer rim of the insertion device. The outer rim of the trumpet comprises a groove 186 which is sized to fit a ring-shaped device. FIG. 15-3 shows a cross-section of the bike-horn shaped insertion device comprising a trumpet and a squeeze bulb. The squeeze bulb comprises a vacuum source and a reservoir for liquid 190, desirably saline. The squeeze bulb is attached to the trumpet.

To pick up a ring-shaped device for insertion on the surface of the eye, the squeeze bulb is squeezed, thereby creating a vacuum seal which picks up and holds the ring-shaped device in the groove of the outer rim of the trumpet. To place the ring-shaped device on the anterior surface of the eye, the trumpet is gently inserted under both eyelids of an eye and the squeeze bulb is gently squeezed, causing the liquid from the squeezed bulb's reservoir to flow through the channels of the trumpet, breaking the vacuum seal between the ring-shaped device and the outer rim of the trumpet. The trumpet is then gently pulled out from underneath the eyelids.

Figures 1, 16:
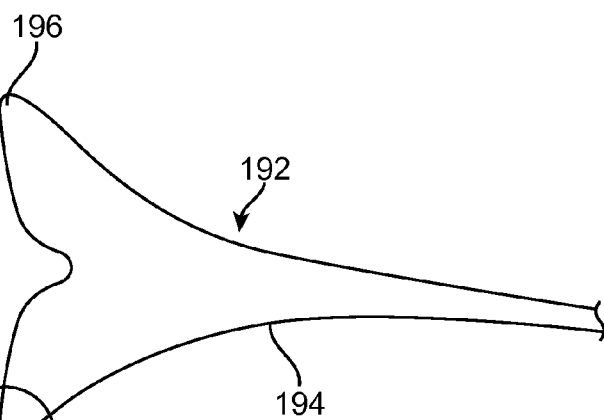
Figures 2, 16:
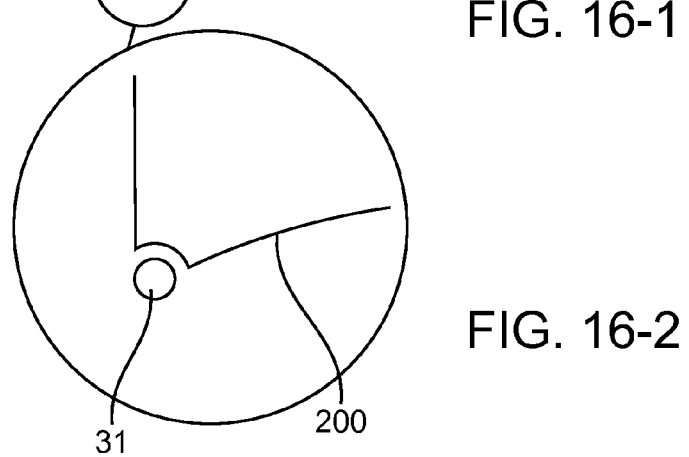
Figures 3, 16:
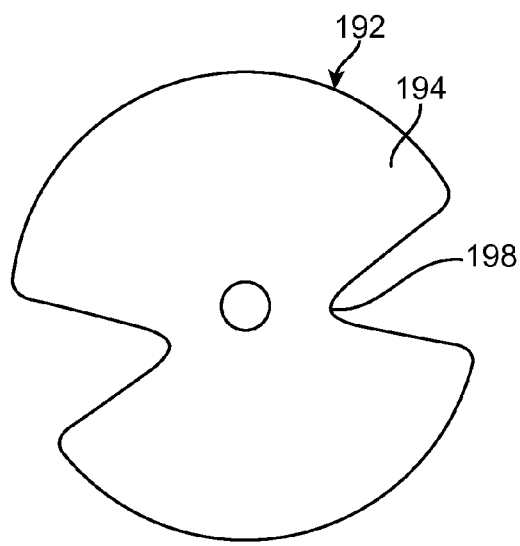
Figures 4, 16:
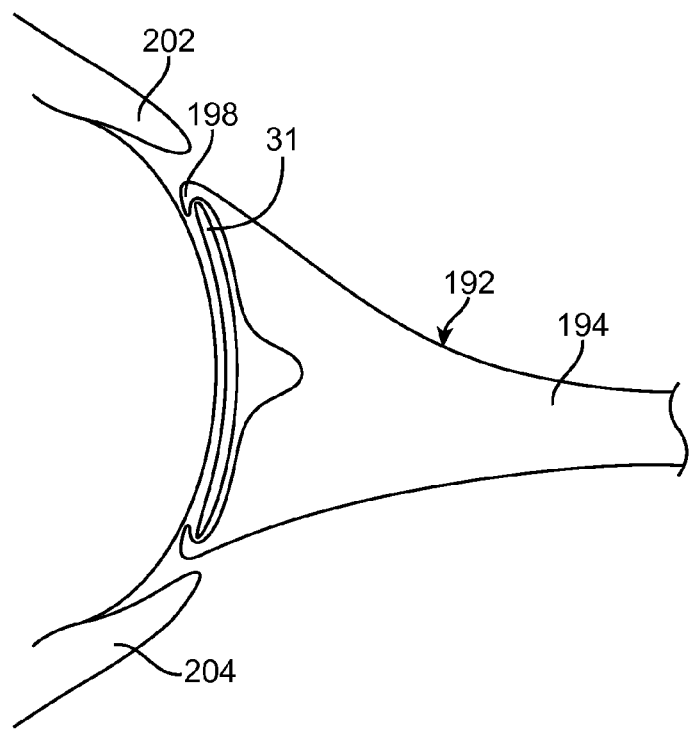
Figures 5, 16:
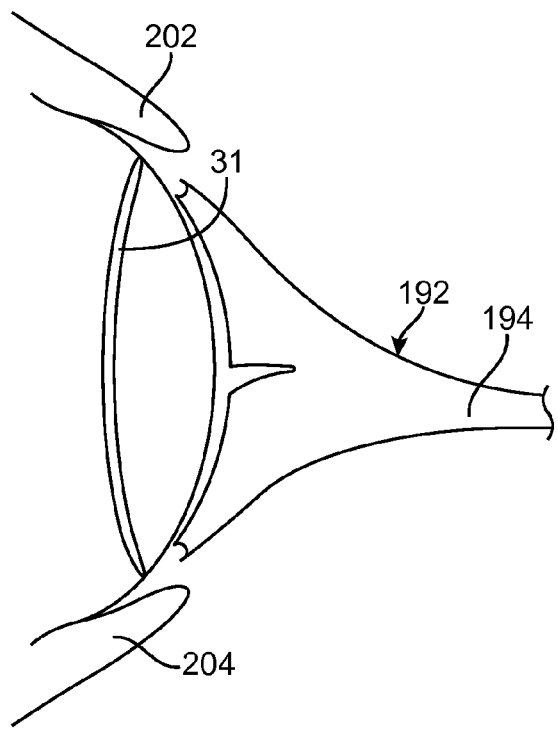

FIGS. 16-1 to 16-6 show an alternative insertion device 192. FIG. 16-1 shows an alternative insertion device 192 comprising a soft flexible cone 194 that supports the ring-shaped device along its outer rim 196 and a method of using it to place an ocular insert on the sclera 8 of the eye 2. FIG. 16-2 shows a close-up view of the outer rim of the delivery device 196. The outer rim comprises a groove 198 designed to fit the ring-shaped ocular insert 31. FIG. 16-3 shows a front view of the insertion device 192 comprising a soft flexible cone. The soft flexible cone comprises two slits 198, to allow the diameter of the cone to be modifiable. FIGS. 16-4 to 16-6 show a method for using the insertion device 192 to insert the ocular insert 31. FIG. 16-4 shows the insertion device 192 loaded with the ring-shaped ocular insert 31 being gently tucked under the top 202 and bottom eyelid 204. FIG. 16-5 shows the soft flexible cone 194 being pinched or pulled, so as to lower the circumference of the cone and release the ring-shaped ocular insert 31 from the outer rim 196 of the cone. FIG. 16-6 shows the ring-shaped ocular insert 31 left in the eye, while the cone 194 is pulled away from under the eyelids.

FIGS. 17-1 to 17-2 show an alternative insertion device. FIG. 17-1 shows the insertion device 206 comprising a flexible curved band 208. As shown in FIG. 17-2, the curved band comprises a curved groove that can support ocular insert 31, while the ocular insert is gently slid behind at least one of the eyelids.

Example 1

Calculation of a Drug's Therapeutically Effective Dosage for an Ocular Insert—Olopatadine The drug Olopatadine, for treatment of allergic conditions, will demonstrate a method that can be used in calculating a drug's therapeutically effective plant-delivered dosage based on a drop-administered treatment regimen for that drug. The calculation method involves the following steps: 1.) determining the number of drops desired per application; 2.) multiplying the number of drops by 30 uL (the volume of one drop); 3.) determining the amount of solid drug per uL; 4.) multiplying the results from step 2 by the result from step 3, to find out the amount of solid drug to be applied to the eye on a daily basis; 5.) multiplying the result in step 4 by the number of days of therapy desired for the particular drug; and 6) multiplying by the efficiency of drug delivery. This final amount will preferably be dispersed from an ocular insert.

Olopatadine is an ophthalmic antihistamine (H 1 -receptor) and mast cell stabilizer. The usual adult dosage for Olopatadine may be, for example, one drop in each affected eye twice a day, when using the 0.1% solution and one drop per day in each affected eye, when using the 0.2% solution.

Estimating use of the 0.1% Olopatadine solution, 1 mL of the drug corresponds to 1 mg of the drug. One drop is 30 uL, which corresponds to 0.03 mL of the solution and 30 ug of Olopatadine. Since the 0.1% solution is applied twice a day, the daily dosage of Olopatadine is 60 ug. Due to the inefficiency of eye drops in drug delivery 90-95% of the Olopatadine applied to the eye is washed out. This leaves only 3-6 ug of Olopatadine in the eye. 3-6 ug per day for 30 days amounts to about 90-180 ug of Olopatadine that may be delivered to one eye within a period of one month.

Example 2

Drug Delivery Procedure & Elution Rate Control for a Hydrophilic Drug—Olopatadine hydrochloride Olopatadine HCl (OH) for ophthalmic applications can be formulated as a 0.2% (2 mg/mL) solution. A single 50 uL drop containing 100 ug of OH may be instilled in the eye once a day for 2 weeks. Estimating 5% availability, this gives a 5 ug/day dose delivered to the cornea, for a total of 70 ug over the course of the 2 week treatment. At least 70 ug in dry form could be loaded into the implant and released into the tear film by partitioning the drug reservoir with a membrane (e.g. HEMA, PVA, PVP, GMA, dialysis tubing of cellulose, etc) or embedding the drug within the implant. The release rate could be controlled by altering the surface area exposed to the tear film to tailor the desired 5 ug/day (0.21 ug/hour), by altering a drug release controlling membrane, or the like. It is again assumed in this calculation that 100% of the targeted dose gets to its target location without being washed out with tear film, and more accurate calculations can be performed using wash-out data.

For both examples, the outside of the implant could be coated for either example with a bolus of the drug for immediate dosing while the hydration process, and thus flux of drug across the membrane or through the reservoir can take place. These coatings could be in solid drug form with a readily dissolvable layer (e.g. starch, sugar) to maintain placement of the solid drug upon the exterior of the implant.

Example 3

Drug Delivery Procedure & Elution Rate Control for a Hydrophobic Drug—Prednisolone Acetate Generally, a 1% Prednisolone acetate suspension (10 mg/mL) is given 2 drops (total of approximately 100 uL volume) 4 times daily for a week. Working with the estimate that 5% of a dose is actually available for absorption into the cornea, this amounts to 20 ug/day of Prednisolone acetate. A week's available dose is then 140 ug. The solubility of Prednisolone acetate in aqueous solutions is approximately 240 ug/mL. At least 140 ug of solid Prednisolone acetate could be loaded into the implant, allowing the Prednisolone acetate to dissolve into the tear layer at a rate of about 0.83 ug/hour. The rate could be controlled by the porosity of the implant as well as the surface area exposed to the tear film.

For these simplified calculations, it has been assumed that 100% of the dose hits the target (the cornea) and is absorbed completely and not lost by tear layer flow away from the cornea. Adjustments can be made based on test data, modeling, or the like.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. An ocular insert for use in an eye, the eye having upper and lower lids extendable along an anterior eye surface with an optical zone therebetween, the insert comprising:

a first structure disposable along the anterior surface of the eye of a patient outside the optical zone of the eye, the first structure comprising an annulus formed of configuration-altering material;

a second structure supported by at least a portion of the first structure, the second structure adapted to provide engagement between the insert and eye tissue surrounding the insert, wherein the second structure has an anterior surface and a posterior surface, the posterior surface configured to contact the anterior surface of the eye, wherein the second structure completely surrounds the portion of the first structure in a cross-section taken from the anterior surface to the posterior surface of the second structure, and wherein the first structure helps maintain the insert in contact with the eye for a plurality of days;

at least one drug disposed on or embedded into the second structure so as to release a safe and therapeutically effective quantity of the drug from the second structure to the eye for each of the plurality of days; and wherein the first structure comprises a configuration-altering, non-biodegradable material that activates after the ocular insert is inserted onto the anterior surface of the eye so as to cause each of the first and the second structures of the ocular insert to reconfigure from an initial, pre-insertion configuration to a second, post-insertion configuration that conforms the first and second structures of the ocular insert to the anterior surface of the eye to maintain the ocular insert in contact with the eye for the plurality of days.

2. The ocular insert of claim 1, wherein the at least one drug is further disposed on or in the first structure.

3. The ocular insert of claim 1, wherein the plurality of days comprises at least 30 days.

4. The ocular insert of claim 1, wherein the drug comprises one or more members selected from the group consisting of: steroids, anti-inflammatories, antibiotics, glaucoma treatment medications, antihistamines, and dry eye medications.

5. The ocular insert of claim 1, wherein the drug comprises one or more members selected from the group consisting of:
   a steroid selected from the group consisting of at least one of glucocorticoids, aprogestins, amineralocorticoids, corticosteroids, cortisone, hydrocortisone, prednisone, prednisolone, methylprednisone, triamcinolone, fluorometholone, dexamethasone, medrysone, betamethasone, loteprednol, fluocinolone, flumethasone, rimexolone mometasone, androgens, testosterone, methyltestosterone, and danazol;
   a non-steroidal anti-inflammatory (NSAID) selected from the group consisting of at least one of piroxicam, aspirin, salsalate, diflunisal, ibuprofen, ketoprofen, nabumetone, piroxicam, naproxen, diclofenac, indomethacin, sulindac, tolmetin, etodolac, ketorolac, oxaprozin, and celecoxib;
   an antibiotic selected from the group consisting of at least one of amoxicillin, penicillin, sulfa drugs, erythromycin, streptomycin, tetracycline, clarithromycin, terconazole, azithromycin, bacitracin, ciprofloxacin, evofloxacin, ofloxacin, levofloxacin, moxifloxacin, gatifloxacin, aminoglycosides, tobramycin, gentamicin, polymyxin B combinations, wherein the polymyxin B combinations are selected from the group consisting of polymyxin B/trimethoprim, polymyxin B/bacitracin, and polymyxin B/neomycin/gramicidin;
   a glaucoma treatment medication selected from the group consisting of at least one of beta-blockers, mitotics, carbonic anhydrase inhibitors, prostaglandins, prostaglandin analogs, seretonergics, muscarinics, dopaminergic agonists, and adrenergic agonists,
      wherein the beta-blockers are selected from the group consisting of timolol, betaxolol, levobetaxolol, and carteolol,
      wherein the miotics are selected from the group consisting of pilocarpine,
      wherein the carbonic anhydrase inhibitors are selected from the group consisting of brinzolamide, and dorzolamide,
      wherein the prostaglandin analogs are selected from the group consisting of travoprost, bimatoprost, and latanoprost, and
      wherein the adrenergic agonists are selected from the group consisting of apraclonidine, and brimonidine;
   an antihistamine and mast cell stabilizer selected from the group consisting of at least one of olopatadine and epinastine;
   an acute care anti-allergenic product selected from the group consisting of at least one of ketorolac tromethamine, ketotifen fumarate, loteprednol, epinastine HCl, emedastine difumarate, azelastine hydrochloride, olopatadine hydrochloride, and ketotifen fumarate;
   a chronic care anti-allergenic product selected from the group consisting of at least one of pemirolast potassium, nedocromil sodium, lodoxamide tromethamine, and cromolyn sodium;
   a dry eye medication selected from the group consisting of cyclosporinel; and
   an anesthetic.

6. The ocular insert of claim 1, wherein the drug is hydrophilic, and wherein the drug is dispersed in a hydrophilic polymer.

7. The ocular insert of claim 1, wherein the drug is hydrophobic, and wherein the insert comprises surfactants to increase the drug solubility.

8. The ocular insert of claim 1, wherein the drug is hydrophobic, and wherein the insert comprises an elution rate decrease material, the elution rate decrease material comprising a coating over the drug, a component of a delivery matrix and/or a coating on the delivery matrix.

9. The ocular insert of claim 1, wherein the annulus has a local thickening along at least one portion of the annulus.

10. The ocular insert of claim 1, wherein the annulus has at least one arc radially offset from the annulus, and a plurality of radial members extending between the at least one arc and annulus.

11. The ocular insert of claim 1, wherein the annulus is a serpentine annulus having radially inward portions interspersed with radially outward portions.

12. The ocular insert of claim 1, wherein the annulus has inner and outer edges, at least one of the edges being atraumatically shaped to avoid sharp-edge irritation of the eye.

13. The ocular insert of claim 1, wherein the annulus has a non-planar eye-engagement surface.

14. The ocular insert of claim 1, further comprising an actuatable delivery instrument having a receptacle for releasably receiving the insert so as to support the insert during positioning of the insert, wherein actuation of the delivery instrument when at least a portion of the insert engages the eye between a sclera and a lid atraumatically releases the insert from the receptacle.

15. An insert as in claim 1, wherein the initial configuration is a first shape and the second configuration is a second shape.

16. An insert as in claim 1, wherein the material of the first structure is thermally activated.

17. An insert as in claim 1, wherein the material of the first structure is activated through heat imparted to the insert through the eye or eyelids.

18. An insert as in claim 1, wherein the drug comprises a prostaglandin analog.

19. An insert as in claim 1, further comprising a coating on at least one of the first and second structures.

20. The ocular insert of claim 1, wherein the insert comprises an elution rate altering material.

21. The ocular insert of claim 20, wherein the drug comprises the elution rate altering material.

22. An insert as in claim 1, wherein the drug comprises at least one of bimatoprost and latanoprost.

23. An insert as in claim 1, wherein the first structure has a circumferential length that forms a diameter sized to fit around and remain outside the cornea of the eye.

24. An insert as in claim 23, wherein the eye tissue surrounding the insert comprises the sclera and/or at least one of the upper and lower eyelids.

25. An insert as in claim 1, wherein the second structure has a cross-sectional shape that is rounded or beveled.

26. An insert as in claim 1, wherein the first structure comprises a material that determines an overall shape of the ocular insert and provides structural support to maintain the ocular insert in contact with the eye for a plurality of days.

27. An insert as in claim 26, wherein the material of the first structure is a polypropylene suture or a nylon suture.

28. An insert as in claim 27, wherein the second structure is a silicone matrix.

29. An insert as in claim 28, wherein the suture threads through an interior of the silicone matrix.

30. An insert as in claim 1, wherein the second structure comprises a plurality of cushioning structures, each cushioning structure completely surrounding a discrete portion of a length of the first structure.

* * * * *